United States Patent
Ly et al.

(10) Patent No.: US 10,370,415 B2
(45) Date of Patent: Aug. 6, 2019

(54) DIVALENT NUCLEOBASE COMPOUNDS AND USES THEREFOR

(71) Applicant: Carnegie Mellon University, Pittsburgh, PA (US)

(72) Inventors: Danith H. Ly, Pittsburgh, PA (US); Suresh Kumar Gopalsamy, Tamilnadu (IN); Arunava Manna, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 634 days.

(21) Appl. No.: 14/782,471

(22) PCT Filed: Apr. 11, 2014

(86) PCT No.: PCT/US2014/033793
§ 371 (c)(1),
(2) Date: Oct. 5, 2015

(87) PCT Pub. No.: WO2014/169206
PCT Pub. Date: Oct. 16, 2014

(65) Prior Publication Data
US 2016/0083434 A1 Mar. 24, 2016

Related U.S. Application Data

(60) Provisional application No. 61/854,138, filed on Apr. 18, 2013, provisional application No. 61/853,758, filed on Apr. 11, 2013.

(51) Int. Cl.
| | |
|---|---|
| C07H 21/02 | (2006.01) |
| C12Q 1/68 | (2018.01) |
| C07K 14/00 | (2006.01) |
| C12Q 1/6809 | (2018.01) |
| C07H 21/04 | (2006.01) |
| C07D 239/47 | (2006.01) |
| C07D 239/54 | (2006.01) |
| C07D 251/16 | (2006.01) |
| C07D 471/04 | (2006.01) |
| C07D 475/08 | (2006.01) |
| C07D 487/04 | (2006.01) |
| C07D 487/16 | (2006.01) |
| C07H 1/06 | (2006.01) |
| G01N 33/53 | (2006.01) |

(52) U.S. Cl.
CPC .......... *C07K 14/003* (2013.01); *C07D 239/47* (2013.01); *C07D 239/54* (2013.01); *C07D 251/16* (2013.01); *C07D 471/04* (2013.01); *C07D 475/08* (2013.01); *C07D 487/04* (2013.01); *C07D 487/16* (2013.01); *C07H 1/06* (2013.01); *C07H 21/04* (2013.01); *C12Q 1/6809* (2013.01); *G01N 33/5308* (2013.01)

(58) Field of Classification Search
CPC .................................................... C07K 14/003

USPC ................................... 536/23.1; 435/6.1
See application file for complete search history.

(56) References Cited

U.S. PATENT DOCUMENTS

| | | | |
|---|---|---|---|
| 5,217,866 | A | 6/1993 | Summerton et al. |
| 6,355,726 | B1 | 3/2002 | Doemling et al. |
| 6,441,130 | B1 | 8/2002 | Egholm et al. |
| 8,053,212 | B1 | 11/2011 | Benner |
| 8,389,703 | B1 | 3/2013 | Benner et al. |
| 8,653,254 | B2 | 2/2014 | Umemoto et al. |
| 2002/0188101 | A1 | 12/2002 | Neilsen et al. |
| 2005/0009041 | A1 | 1/2005 | Buchardt et al. |
| 2006/0160751 | A1 | 7/2006 | McGuire |
| 2011/0028337 | A1 | 2/2011 | Bradley et al. |

FOREIGN PATENT DOCUMENTS

| | | |
|---|---|---|
| WO | 2004024757 A2 | 3/2004 |
| WO | 2012138955 A2 | 10/2012 |

OTHER PUBLICATIONS

Adleman, "Molecular Computation of Solution to Combinatorial Problems", Science, 1994, vol. 266, pp. 1021-1024.
Aldaye et al., "Assembling Materials with DNA as the Guide", Science, 2008, vol. 321, pp. 1795-1799.
Ashley, "Modeling, Synthesis, and Hybridization Properties of (L)-Ribonucleic Acid", Journal of the American Chemical Society, 1992, vol. 114:25, pp. 9731-9736.
Avitabile et al., "γsulphate PNA (PNA S): Highly Selective DNA Binding Molecule Showing Promising Antigene Activity", Peptide Nucleic Acid analogues, 2012, vol. 7:5, pp. 1-10.
Bahal et al., "Sequence-Unrestricted, Watson-Crick Recognition of Double Helical B-DNA by (R)-MiniPEG- γPNAs", ChemBioChem, 2012 vol. 13, pp. 56-60.
Bahal et al., "Single-Stranded γPNAs for In Vivo Site-Specific Genome Editing via Watson-Crick Recognition", Current Gene Therapy, 2014, vol. 15, pp. 331-342.
Ban et al., "The Complete Atomic Structure of the Large Ribosomal Subunit at 2.4 A Resolution", Science, 2000, vol. 289, pp. 905-920.
Bath et al., "DNA nanomachines", Nature Nanotechnology, 2007, vol. 2, pp. 275-284.
Beck et al., "Artificial DNA: methods and applications", 2003, CRC Press, Boca Raton, vol. 2003 pp. 91-115.

(Continued)

*Primary Examiner* — Jezia Riley
(74) *Attorney, Agent, or Firm* — The Webb Law Firm

(57) ABSTRACT

Described herein are novel divalent nucleobases that each bind two nucleic acid strands, matched or mismatched when incorporated into a nucleic acid or nucleic acid analog backbone (a genetic recognition reagent, or genetic recognition reagent). In one embodiment, the genetic recognition reagent is a peptide nucleic acid (PNA) or gamma PNA (?PNA) oligomer. Uses of the divalent nucleobases and monomers and genetic recognition reagents containing the divalent nucleobases also are provided.

47 Claims, 20 Drawing Sheets

(56) References Cited

OTHER PUBLICATIONS

Berry et al., "Crystal structure of the HCV IRES central domain reveals strategy for start-codon positioning", Structure, 2011, vol. 19, pp. 1456-1466.
Braasch et al., "Synthesis, Analysis, Purification, and Intracellular Delivery of Peptide Nucleic Acids", Methods, 2001, vol. 23, pp. 97-107.
Butcher et al., "The Molecular Interactions That Stabilize RNA Tertiary Structure: RNA Motifs, Patterns, and Networks", Accounts of Chem. Res., 2011, vol. 44:12, pp. 1302-1311.
Chen et al., "Synthesis from DNA of a molecule with the connectivity of a cube", Letters to Nature, 1991, vol. 350, pp. 631-633.
Chen, "Expanding the Rule Set of DNA Circuitry with Associative Toehold Activation", Journal of the American Chemical Society, 2012, vol. 134, pp. 263-271.
Chin et al., "Correction of a splice-site mutation in the beta-globin gene stimulated by triplex-forming peptide nucleic acids," PNAS, 2008, vol. 15:36, p. 13514-13519.
Choi et al., "Programmable in situ amplification for multiplexed imaging of mRNA expression", Nature Biotechnology, 2010, vol. 28:11, pp. 1208-1214.
Choi et al., "Next-Generation in Situ Hybridization Chain Reaction: Higher Gain, Lower Cost, Greater Durability", ACS Nano, 2014. vol. 8:5. pp. 4284-4294.
Costantino et al., "tRNA-mRNA mimicry drives translation initiation from a viral IRES", Nat. Struct. Mol. Biol., 2008, vol. 15:1, pp. 57-64.
Dawson et al., "Synthesis of Proteins by Native Chemical Ligation", Science, 1994, vol. 266:5186, pp. 776-779.
De Costa et al., "Evaluating the Effect of Ionic Strength on Duplex Stability for PNA Having Negatively or Positively Charged Side Chains", PLOS ONE, 2013, vol. 8:3, pp. 1-8.
De Francesco et al., "Challenges and successes in developing new therapies for hepatitis C", Nature, 2005, 436:18, pp. 953-960.
Delebecque et al., "Organization of Intracellular Reactions with Rationally Designed RNA Assemblies", Science, 2011, vol. 333, pp. 470-474.
Demidov et al., "Stability of peptide nucleic in human serum and cellular extracts", Biochemical Pharacology, 1994, vol. 48:6, pp. 1310-1313.
Dezhenkov et al., "Synthesis of anionic peptide nucleic acid oligomers including γ-carboxyethyl thymine monomers", Mendeleev Commun., 2015, vol. 25, pp. 47-48.
Dibrov et al., "Structure of a hepatitis C virus RNA domain in complex with a translation inhibitor reveals a binding mode reminiscent of riboswitches", PNAS, 2012, vol. 109:14, pp. 5223-5228.
Dietz et al., "Folding DNA into Twisted and Curved Nanoscale Shapes", Science, 2009, vol. 325. pp. 725-730.
Dirks et al., "Triggered amplification by hybridization chain reaction", PNAS, 2004, vol. 101:43, pp. 15275-15278.
Dose et al., "Convergent Synthesis of Peptide Nucleic Acids by Native Chemical Ligation", Organic Letters, 2005, vol. 7:20, pp. 4365-4368.
Doudna, "Structural genomics of RNA", Nature Structural Biology, 2000, pp. 954-956.
Douglas et al., "A Logic-Gated Nanorobot for Targeted Transport of Molecular Payloads", Science, 2012, vol. 335, pp. 831-834.
Dragulescu-Andrasi et al.; "A Simple Gamma-Backbone Modification Preorganizes Peptide Nucleic Acid into a Helical Structure", JACS, 2006, vol. 128:31, 10258-10267.
Dueholm et al., "Synthesis of Peptide Nucleic Acid Monomers Containing the Four Natural Nucleobases: Thymine, Cytosine, Adenine, and Guanine and Their Oligomerization", Journal of Organic Chemistry, 1994, vol. 59:19, pp. 5767-5773.
Englund et al., "Synthesis of γ-Substituted Peptide Nucleic Acids: A New Place to Attach Fluorophores without Affecting DNA Binding", Organic Letters, 2005, vol. 7:16, pp. 3465-3467.
Falkiewicz et al., "Synthesis of achiral and chiral peptide nucleic acid (PNA) monomers using Mitsunobu reaction", Tetrahedron, 2001, vol. 57, pp. 7909-7917.
Fischer, Ber. Dtsch. Chem. Ges., 1894, vol. 27, pp. 2985-2993.
Frezza et al., "Modular Multi-Level Circuits from Immobilized DNA-Based Logic Gates", Journal of American Chemical Society, 2007. vol. 129, pp. 14875-14879.
Fujimori et al., "Enantio-DNA Recognizes Complementary RNA but Not Complementary DNA", Journal of American Chemical Society, 1990, vol. 112, pp. 7436-7438.
Genot et al., "Reversible Logic Circuits Made of DNA", Journal of American Chemical Society, 2011, vol. 133, pp. 20080-20083.
Gerling et al., "Dynamic DNA devices and assemblies formed by shape-complementary, non-base pairing 3D cmponents", Science, 2015, vol. 347:6229, pp. 1446-1452.
Hameed, "DNA Computation Based Approach for Enhanced Computing Power", Int. J. Emerg. Sci., 2011, vol. 1:1, pp. 31-37.
Han et al., "DNA Origami with Complex Curvatures in Three-Dimensional Space", Science, 2011, vol. 332, pp. 342-346.
He et al., "Strand-Invasion of Extended, Mixed-Sequence B-DNA by gammaPNAs", Journal of American Chemical Society, 2009, vol. 131:34, pp. 12088-12090.
Hirao et al., "Natural versus Artificial Creation of Base Pairs in DNA: Origin of Nucleobases from the Perspectives of Unnatural Base Pair Studies", Accounts of Chemical Research, 2012, vol. 45:12, pp. 2055-2065.
Huang et al., "Preparation and Determination of Optical Purity of γ-Lysine Modified Peptide Nucleic Acid Analogues", Archives of Pharmacal Research, 2012, vol. 35:3, pp. 517-522.
Immordino et al., "Stealth liposomes: review of the basic science, rationale, and clinical applications, existing and potential", International Journal of Nanomedicine, 2006, vol. 1:3, pp. 297-316.
Janowski et al., "Inhibiting transcription of chromosomal DNA with antigene peptide nucleic acids", Nature Chemical Biology, 2005, vol. 1:4, pp. 210-215.
Johnston et al., "An HIV Vaccine-Challenges and Prospects", New England Journal of Medicine, 2008, vol. 359:9 pp. 888-890.
Jones et al., "Programmable materials and the nature of the DNA bond", Science, 2015, vol. 347:6224, pp. 840-853.
Kadhane et al., "Strong coupling between adenine nucleobases in DNA single strands revealed by circular dichroism using synchrotron radiation", Physical Review, 2008, pp. 021901-1-021901-4.
Ke et al., "Three-Dimensional Structures Self-Assembled from DNA Bricks", Science, 2012, vol. 338, pp. 1177-1183.
Arambula et al., "A simple ligand that selectively targets CUG trinucleotide repeats and inhibits MBNL protein binding", PNAS, Sep. 22, 2009, pp. 16068-16073, vol. 106, No. 38.
Artigas et al., "Synthesis of Janus Compounds for the Recognition of G-U Mismatched Nucleobase Pairs", The Journal of Organic Chemistry, 2013, pp. 10666-10677, vol. 78.
Branda et al., "Janus Wedges: a new approach towards nucleobase-pair recognition", Chem. Commun., 1996, pp. 2442-2444, vol. 21.
Chen et al., "Formation and Stability of a Janus-Wedge Type of DNA Triplex", Journal of American Chemical Society, 2004, pp. 70-71, vol. 126.
Chen et al., "A Janus-Wedge DNA Triplex with A-W1-T and G-W2-C Base Triplets", Journal of American Chemical Society, 2008, pp. 13190-13191, vol. 130.
Robinson et al., "Modular Riboswitch Toolsets for Synthestic Genetic Control in Diverse Bacterial Species" Journal of American Chemical Society, 2014, pp. 10615-10624, vol. 136.
Shin et al., "Bifacial Nucleoside as a Surrogate for Both T and A in Duplex DNA", Journal of American Chemical Society, 2011, pp. 6926-6929, vol. 133.
Zeng et al., "Discrete Assembly of Synthetic Peptide-DNA Triplex Structures from Polyvalent Melamine-Thymine Bifacial Recognition", Journal of the American Chemical Society, 2012, pp. 832-835, vol. 134.
Zhao et al., "Synthesis of a Complete Janus-type Guanosine-Cytosine Base and Its 2'-Deoxyribonucleoside", Chem. Lett., 2011, pp. 684-686, vol. 40.
Stratagene Catalog, 1988, p. 39.

(56) References Cited

OTHER PUBLICATIONS

Felix et al, "Covalent Linkage of Melamine and Cyanurate Improves the Thermodynamic Stability of Hydrogen-Bonded Double Rosettes in Polar Solvents", Eur. J. Org. Chem., 2003, pp. 1463-1474.
Kleiner et al., "DNA-Templated Polymerization of Side-Chain-Functionalized Peptide Nucleic Acid Aldehydes", Journal of American Chemical Society, 2008, vol. 130, pp. 4646-4659.
Konrad et al., "Synthese and Eigenschaften von 2.4-Diamino-6-und-7-oxo-dihydropteridinen", Chem. Ber., 1970, vol. 103, pp. 735-744.
Koppelhus et al., "Cell-Dependent Differential Cellular Uptake of PNA, Peptides, and PNA-Peptide Conjugates", Antisense & Nucleic Acid Drug Development, 2002, vol. 12, pp. 51-63.
Kosynkina et al., "A Convenient Synthesis of Chiral Peptide Nucleic Acid (PNA) Monomers", Tetrahedron Letters, 1994, vol. 35:29, pp. 5173-5176.
Kuhn et al., "Hybridization of DNA and PNA Molecular Beacons to Single-Stranded and Double-Stranded DNA Targets", Journal of American Chemical Society, 2002, vol. 124:6, pp. 1097-1103.
Kumar et al., "Conformationally Constrained PNA Analogues: Structural Evolution toward DNA/RNA Binding Selectivity", Accounts of Chemical Research, 2005, vol. 38:5, pp. 404-412.
Kuzyk et al., "DNA-based self-assembly of chiral plasmonic nanostructures with tailored optical response", Nature, 2012, vol. 483, pp. 311-314.
Li et al., "Controlled assembly of dendrimer-like DNA", Nature Materials, 2004, vol. 3, pp. 38-42.
Li et al., "DNA-Templated Organic Synthesis: Nature's Strategy for Controlling Chemical Reactivity Applied to Synthetic Molecules", Angewandte Chemie International Edition, 2004, vol. 43, pp. 4848-4870.
Liedl et al., "DNA-based nanodevices", Nanotoday, 2007, vol. 2:2, pp. 36-41.
Lin et al., "Whole Genome Shotgun Optical Mapping of Deinococcus Radiodurans", Science, 1999, vol. 285, pp. 1558-1562.
Lund et al., "Molecular robots guided by prescriptive landscapes", Nature, 2010, vol. 465, pp. 206-210.
Manna et al. "Synthesis of optically pure γPNA monomers: a comparative study", Tetrahedron, 2015, vol. 71, pp. 3507-3514.
Michaelis et al., "Amplification by nucleic acid-templated reactions", Organic & Biomolecular Chemistry, 2014, vol. 12, pp. 2821-2833.
Mir, "Sequencing Genomes: From Individuals to Populations", Briefings in Functional Genomics and Proteomics., 2009, vol. 8:5, pp. 367-378.
Mitra et al., "Aminomethylene Peptide Nucleic Acid (am-PNA): Synthesis, Regio-/Stereospecific DNA Binding, and Differential Cell Uptake of (α/γ,R/S)am-PNA Analogues", The Journal of Organic Chemistry, 2012, vol. 77, pp. 5696-5704.
Moradpour et al., "Replication of hepatitis C virus," Nature Reviews Microbiology, 2007, vol. 5, pp. 453-463.
Morens et al., "The challenge of emerging and re-emerging infectious diseases", Nature, 2004, vol. 430, pp. 242-249 and corrections, Nature, 2010, vol. 463, pp. 122.
Nielsen et al., "Sequence-Selective Recognition of DNA by Strand Displacement with a Thymine-Substituted Polyamide", Science, 1991, vol. 254, pp. 1497-1500.
Nielsen, "Peptide Nucleic Acid. A Molecule with Two Identities", Acc. Chem. Res., 1999, vol. 32, pp. 624-630.
Nielsen, "Addressing the challenges of cellular delivery and bioavailabilityof peptidenucleic acids (PNA)", Quarterly Reviews of Biophysics, 2005, vol. 38:4, pp. 345-350.
Nissen et al., "RNA tertiary interactions in the large ribosomal subunit: The A-minor motif", PNAS, 2001, vol. 98:9, pp. 4899-4903.
Niu et al., "AApeptides as a new class of antimicrobial agents", Organic & Biomolecular Chemistry, 2013, vol. 11, pp. 4283-4290.
Noller, "RNA Structure: Reading the Ribosome", Science, 2005, vol. 309, pp. 1508-1514.
Oh et al., "Excimer-Based Peptide Beacons: A Convenient Experimental Approach for Monitoring Polypeptide-Protein and Polypeptide-Oligonucleotide Interactions", Journal of American Chemical Society, 2006, vol. 128, pp. 14018-14019.
Omabegho et al., "A Bipedal DNA Brownian Motor with Coordinated Legs", Science, 2009, vol. 324, pp. 67-71.
Pfingsten et al., "Structural Basis for Ribosome Recruitment and Manipulation by a Viral IRES RNA", Science, 2006, vol. 314:5804, pp. 1450-1454.
Piccirilli et al., "Enzymatic incorporation of a new base pair into DNA and RNA extends the genetic alphabet", Nature, 1990, vol. 343, pp. 33-37.
Pinheiro et al., "Challenges and opportunities for structural DNA nanotechnology", Nature Nanotechnology, 2011, vol. 6:12, pp. 763-772.
Poehlsgaard et al., "The Bacterial Ribosome as a Target for Antibiotics", Nature Reviews Microbiology, 2005, vol. 3, pp. 870-881.
Qian et al., "Scaling Up Digital Circuit Computation with DNA Strand Displacement Cascades", Science, 2011, vol. 332, pp. 1196-1201.
Rajwanshi et al., "LNA stereoisomers: xylo-LNA {β-D-xylo configured locked nucleic acid} and α-L-LNA (α-L-ribo configured locked nucleic acid)", Chem. Commun, 1999, pp. 1395-1396.
Ranasinghe et al., "Linear fluorescent oligonucleotide probes with an acridine quencher generate a signal upon hybridization", Chem. Commun., 2001, pp. 1480-1481.
Rapireddy et al., "Strand Invasion of Mixed-Sequence B-DNA by Acridine-Linked, gamma-Peptide Nucleic Acid (gamma-PNA)", JACS, 2007, vol. 129, pp. 15596-15600.
Rapireddy et al., "Strand-Invasion of Mixed-Sequence, Double-Helical B-DNA by gamma-Peptide Nucleic Acids Containing G-Clamp Nucelobases under Physiological Conditions," Biochemistry, 2011, vol. 50, pp. 3913-3918.
Ratilainen et al., "Hybridization of Peptide Nucleic Acid", Biochemistry, 1998, vol. 37, pp. 12331-12342.
Ratilainen et al., "Thermodynamics of Sequence-Specific Binding of PNA to DNA", Biochemistry, 2000, vol. 39, pp. 7781-7791.
Rothemund, "Folding DNA to create nanoscale shapes and patterns", Nature, 2006, vol. 440, pp. 297-302.
Sahoo et al., "Pyrene Excimer Fluorescence: A Spatially Sensitive Probe to Monitor Lipid-Induced Helical Rearrangement of Apolipophorin III", Biochemistry, 2000, vol. 39, pp. 6594-6601.
Sahu et al., "Synthesis of Conformationally Preorganized and Cell-Permeable Guanidine-Based gamma-Peptide Nucleic Acids (gammaGPNAs)", J. Org. Chem., 2009, vol. 74, pp. 1509-1516.
Sahu et al., "Synthesis and Characterization of Conformationally Preorganized, MiniPEG-Containing γPNAs with Superior Hbridization Properties and Water Solubility", J. Org. Chem., 2011, vol. 76:14, pp. 5614-5627.
Seelig et al., "Enzyme-Free Nucleic Acid Logic Circuits", Science, 2006, vol. 314, pp. 1585-1588.
Seitz, "Solid-Phase Synthesis of Doubly Labeled Peptide Nucleic Acids as Probes for the Real-Time Detection of Hybridization", Angewandte Chemie International Edition, 2000, vol. 39:18, pp. 3249-3252.
Serpell et al., "Precision Polymers and 3D DNA Nanostructures: Emergent Assemblies from New Parameter Space", Journal of the American Chemical Society, 2014, vol. 136, pp. 15767-15774.
Severcan et al., "A polyhedron made of tRNAs", Nature Chemistry, 2010, vol. 2, pp. 772-779.
Sforza et al., "Chiral Peptide Nucleic Acids (PNAs):Helix Handedness and DNA Recognition", European Journal of Organic Chemistry, 1999, pp. 197-204.
Silverman et al., "Detecting RNA and DNA with Templated Chemical Reactions", Chemical Reviews, 2006, vol. 106, pp. 3775-3789.
Singer et al., "Electronic Barcoding of a Viral Gene at the Single-Molecule Level", Nano Letters, 2012, vol. 12, pp. 1722-1728.
Smalley et al., "Fluorescence of covalently attached pyrene as a general RNA folding probe", Nucleic Acids Research, 2006, vol. 34:1, pp. 152-166.
Stanzle et al., "FifteenYears of Cell-Penetrating,Guanidinium-Rich Molecular Transporters: Basic Sciene", Accounts of Chemical Research, 2013, vol. 46:12, pp. 2944-2954.

(56) References Cited

OTHER PUBLICATIONS

Sugiyama et al., "Chiral Peptide Nucleic Acids with a Substituent in the N-(2-Aminoethy)glycine Backbone", Molecules, 2013, vol. 18, pp. 287-310.
Tackett et al., "Non-Watson-Crick interactactions between PNA and DNA inhibit the ATPase activity of bacteriophage T4 Dda helicase", Nucleic Acids Research, 2002, vol. 30:4, pp. 950-957.
Tedeschi et al., "Synthesis of new chiral PNAs bearing a dipeptide-mimic monomer with two lysine-derived stereogenic centres", Tetrahedron Letters, 2005, vol. 46, pp. 8395-8399.
Theimer et al., "Structure of the Human Telomerase RNA Pseudoknot Reveals Conserved Tertiary Interactions Essential for Function", Molecular Cell, 2005, vol. 17, pp. 671-682.
Thurner et al., "Conserved RNA secondary structures in Flaviviridae genomes", Journal of General Virology, 2004, vol. 85, pp. 1113-1124.
Tomac et al., "Ionic Effects on the Stability and Conformation of Peptide Nucleic Acid Complexes", Journal of the American Chemical Society, 1996, vol. 118, pp. 5544-5552.
Wan et al., "Understanding the transcriptome through RNA structure", Nature Review Genetics, 2011, vol. 12, pp. 641-655.
Watts et al., "Architecture and secondary structure of an entire HIV-1 RNA genome", Nature, 2009, vol. 460, pp. 711-719.
Wei et al., "Complex shapes self-assembled from single-stranded DNA tiles", Nature, 2012, vol. 485, pp. 623-627.
Wengel, "Synthesis of 3'-C- and 4'-C-Branched Oligodeoxynucleotides and the Development of Locked Nucleic Acid (LNA)", Accounts of Chemical Research, 1999, vol. 32:4, pp. 301-310.
Wimberly et al., "Structure of the 30S ribososmal subunit", Nature, 2000, vol. 407, pp. 327-339.
Winssinger, "Nucleic Acid-programmed Assemblies: Translating Instruction into Function in Chemical Biology", Chimia, 2013, vol. 67:5, pp. 340-348.
Wittung et al., "DNA-like double helix formed by peptide nucleic acid", Nature, 1994, vol. 368. pp. 561-563.
Wittung et al., "Induced Chirality in PNA-PNA Duplexes", Journal of the American Chemical Society, 1995, vol. 117:41, pp. 10167-10173.
Wu et al., "Synthesis of chiral peptide nucleic acids using Fmoc chemistry", Tetrahedron, 2001, vol. 57, pp. 8107-8113.
Yan et al., "DNA-Templated Self-Assembly of Protein Arrays and Highly Conductive Nanowires", Science, 2003, vol. 301, pp. 1882-1884.
Yang et al., "Light-switching excimer probes for rapid protein monitoring in complex biological fluids", PNAS, 2005, vol. 102:48, pp. 17278-17283.
Yeh et al., "Crystal Structure of Chiral gammaPNA with Complementary DNA Strand: Insights into the Stability and Specificity of Recognition and Conformational Preorganization", Journal of the American Chemical Society, 2010, vol. 132:31, pp. 10717-10727.
Yurke et al., "A DNA-fuelled molecular machine made of DNA", Nature, 2000, vol. 406, pp. 605-608.
Zhang et al., "Dynamic DNA nanotechnology using strand displacement reactions", Nature Chemistry, 2011, vol. 3, pp. 103-113.
Zhou et al., "Novel Binding and Efficient Cellular Uptake of Guanidine-Based Peptide Nucleic Acids (GPNA)", Journal of the American Chemical Society, 2003, vol. 125, pp. 6878-6879.

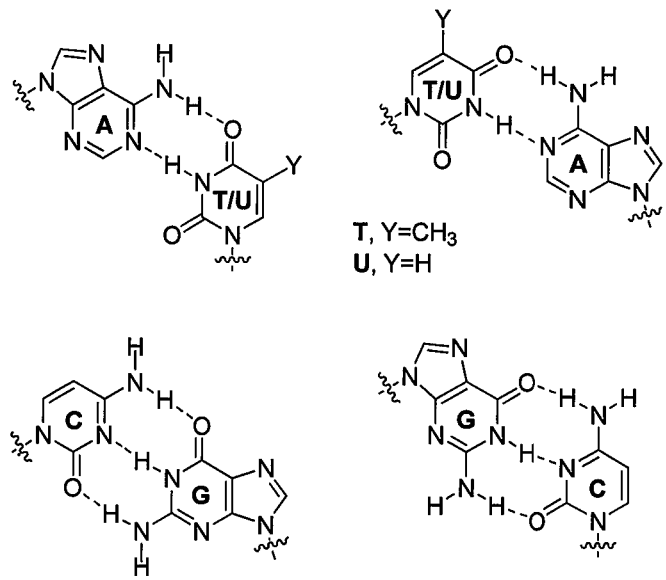
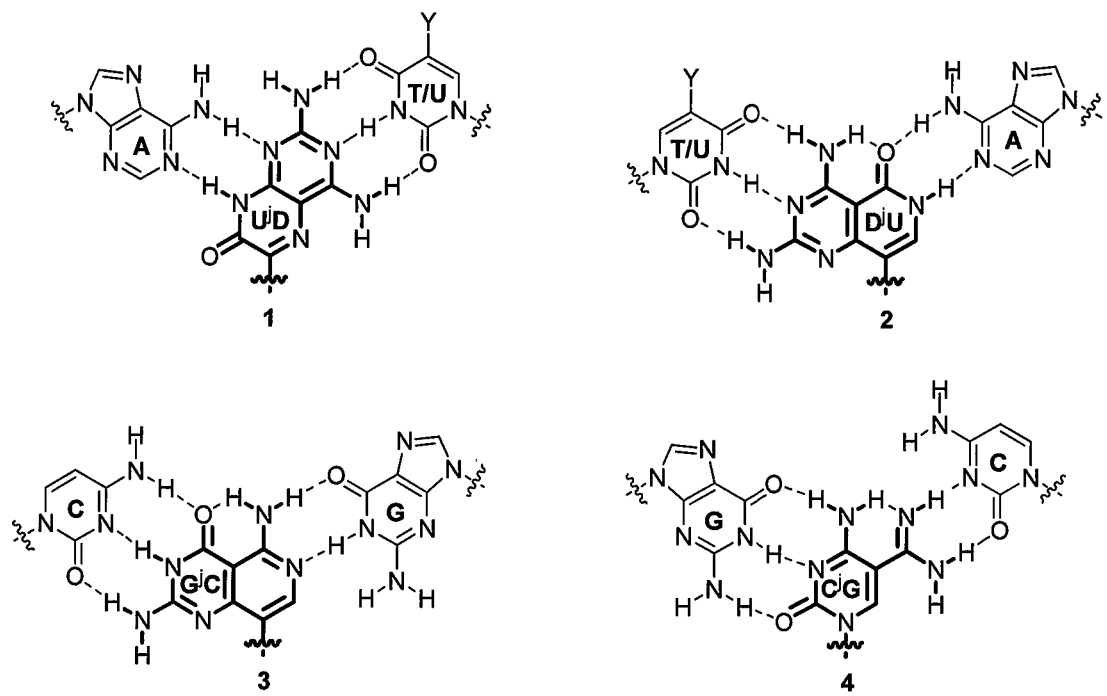
Fig. 1A
Fig. 1B

JB9

JB10

JB14

JB15

JB16

DIVALENT NUCLEOBASE COMPOUNDS AND USES THEREFOR

CROSS REFERENCE TO RELATED APPLICATIONS

This application is a national phase of International Application No. PCT/US2014/033793 filed Apr. 11, 2014, and claims the benefit of copending U.S. Provisional Application Nos. 61/853,758 filed Apr. 11, 2013, and 61/854,138 filed Apr. 18, 2013, each of which is incorporated herein by reference in its entirety.

STATEMENT REGARDING FEDERAL FUNDING

This invention was made with government support under Grant No. CHE-1012467 awarded by the National Science Foundation. The government has certain rights in this invention.

BACKGROUND

1. Field of the Invention

Described herein are nucleobases, polymer monomers comprising the nucleobases and nucleic acids and analogs thereof comprising the nucleobases. Also described herein are methods of use of the nucleobases, polymer monomers comprising the nucleobases and nucleic acids and analogs thereof comprising the nucleobases.

2. Description of the Related Art

For most organisms, genetic information is encoded in double-stranded DNA in the form of Watson-Crick base-pairing—in which adenine (A) pairs with thymine (T) and cytosine (C) with guanine (G). Depending on which set of this genetic information is decoded through transcription and translation, the developmental program and physiological status will be determined. Development of molecules that can be tailor-designed to bind sequence-specifically to any part of this genetic biopolymer (DNA or RNA), thereby enabling the control of the flow of genetic information and assessment and manipulation of the genome's structures and functions, is important for biological and biomedical research in the effort to unravel the molecular basis of life, including molecular tools for basic research in biology. This effort is also important for medicinal and therapeutic applications for the treatment and detection of genetic diseases.

Compared to proteins, RNA molecules are easier to target because they are made up of just four building blocks (A, C, G, U), whose interactions are defined by the well-established rules of Watson-Crick base-pairing. Compared to standard, double-stranded DNA (or RNA), the secondary structures of RNA are generally thermodynamically less stable and, thus, energetically less demanding for binding because, in addition to being canonical (perfectly-matched) base-pairs, many of them are noncanonical (mismatched) and contain single-stranded loops, bulges, and junctions. The presence of these local interacting domains is essential for 'tertiary' interactions and assembly of the secondary structures into compact three-dimensional shapes. As such, slight variations in the interaction patterns or bonding strengths within these regions will have a profound effect on the overall three-dimensional folding patterns of RNA. Thus, molecules that can be used to modulate RNA interactions and thereby interfere with the RNA folding behaviors are important as molecular tools for assessing RNA functions, as well as therapeutic and diagnostic reagents.

RNA-RNA and RNA-protein interactions play key roles in gene regulation, including replication, translation, folding and packaging. The ability to selectively bind to regions within the secondary structures of RNA will often modify their physiological functions.

SUMMARY

Provided herein are reagents that can be used to target double-stranded nucleic acid sequences, including RNA secondary structures and mismatches. The reagents are relatively small in size, can be manufactured in large quantity and more cheaply using solution-phase methodology, and are readily taken-up by cells. They are especially appealing for targeting rapidly evolving sites, such as those associated with the pathology of cancer, bacterial and viral infection, because the described recognition scheme is modular in nature and can be readily modified to match the newly emerged sequence at will. This is a niche that is not currently fulfilled by small-molecule drugs, or traditional antisense or antigene targeting approach.

"Janus" nucleobases (JBs) are described herein. Janus nucleobases are capable of forming directional hydrogen bonding interactions with both strands of the DNA and/or RNA double helix whether or not mismatches are present. This platform has applications in basic research in biology and biotechnology, diagnostics and therapeutics. In one embodiment, the nucleobases are attached to a γPNA backbone, integrating conformational preorganization inherent in the backbone of γPNA with improvements in hydrogen-bonding and base-stacking capabilities, a common property of the Janus nucleobases described herein, into a single system. Unlike the natural nucleobases, which can only hybridize to one strand of the DNA or RNA double helix, these 'Janus' nucleobases can hybridize to both strands of the DNA or RNA targets. This method and platform can affect the regulation of gene expression and modulation of nucleic acid interactions—as molecular tools for basic research as well as therapeutic and diagnostic reagents for the treatment and detection of genetic diseases and pathogenic infections.

Provided herein is a genetic recognition reagent, such as a nucleic acid, gamma peptide nucleic acid (γPNA) or other nucleic acid. The genetic recognition reagent comprises a plurality of nucleobase residues attached to a nucleic acid or nucleic acid analog backbone. At least one nucleobase is a divalent nucleobase chosen from the nucleobases described in Table A, below, in which each instance of R1 is, independently, a protecting group or H and X is CH or N. Non-limiting examples of protecting groups include: methyl, formyl, ethyl, acetyl, anisyl, benzyl, benzoyl, carbamate, trifluoroacetyl, diphenylmethyl, triphenylmethyl, N-hydroxysuccinimide, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethozybenzyl, p-methoxyphenyl, 4-toluenesulfonyl, p-nitrobenzenesulfonates, 9-fluorenylmethyloxycarbonyl, 2-nitrophenylsulfenyl, 2,2,5,7,8-pentamethyl-chroman-6-sulfonyl, and p-bromobenzene sulfonyl. In certain embodiments, the backbone is chosen from one of a DNA, RNA, peptide nucleic acid (PNA), phosphorothioate, locked nucleic acid, unlocked nucleic acid, 2'-O-methyl-substituted RNA, morpholino nucleic acid, threose nucleic acid, or glycol nucleic acid backbone, or any combination thereof. In one embodiment, the backbone is a peptide nucleic acid (PNA) backbone, for example and without limitation a γPNA backbone. The backbone is optionally PEGylated, with one or more PEG moieties of two to fifty (—O—CH$_2$—CH$_2$—) residues. An exemplary γPNA backbone includes a backbone monomer residue that is

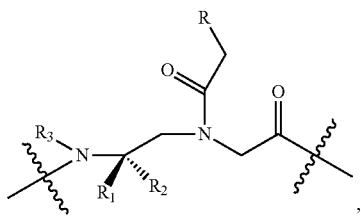

where R1, R2 and R3 are, independently, H, amino acid side chains, linear or branched (C$_1$-C$_8$)alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$) cycloalkyl, (C$_3$-C$_8$)aryl(C$_1$-C$_6$)alkylene, (C$_3$-C$_8$)cycloalkyl (C$_1$-C$_6$)alkylene, PEGylated moieties of the preceding comprising from 1 to 50 (—O—CH$_2$—CH$_2$—) residues, —CH$_2$—(OCH$_2$—CH$_2$)$_q$OP$_1$, —CH$_2$—(OCH$_2$—CH$_2$)$_q$—NHP$_1$, —CH$_2$—(OCH$_2$—CH$_2$-0)$_q$—SP$_1$ and —CH$_2$—(SCH$_2$—CH$_2$)$_q$—SP$_1$, —CH$_2$—(OCH$_2$—CH$_2$)$_r$—OH, —CH$_2$—(OCH$_2$—CH$_2$)$_r$—NH$_2$, —CH$_2$—(OCH$_2$—CH$_2$)$_r$—NHC(NH)NH$_2$, or —CH$_2$—(OCH$_2$—CH$_2$)$_r$—S—S[CH$_2$CH$_2$]$_s$NHC(NH)NH$_2$, where P$_1$ is selected from the group consisting of H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl (C$_1$-C$_6$)alkylene and (C$_3$-C$_8$)cycloalkyl(C$_1$-C$_6$)alkylene; q is an integer from 0 to 10, inclusive; r and s are each independently integers from 1 to 50, inclusive; where R1 and R2 are different and one of R1 or R2 is H. In one example R2 is H, R1 is an amino acid side chain that is optionally PEGylated, with one or more PEG moieties of one to twelve (—O—CH$_2$—CH$_2$—) residues. The nucleobases are arranged in certain embodiments in a sequence complementary to a target sequence of a nucleic acid. In one embodiment, the genetic recognition reagent has 3 to 25 nucleobases. In one embodiment of the composition described above the genetic recognition reagent has the structure:

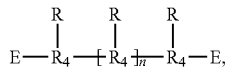

where each instance of R4 is a backbone monomer residue and each instance of R is a nucleobase, where at least one instance of R the divalent nucleobase, E are independently end groups, and "n" is zero or a positive integer ranging from 1 to 48, in which the sequence of nucleobases R is complementary to a target sequence of a nucleic acid. In another embodiment the divalent nucleobases are, independently chosen from JB1, JB2, JB3 and JB4. In yet another embodiment, all instances of R1 are H.

Also provided is a monomer for production of a genetic recognition reagent comprising a backbone monomer for a genetic recognition reagent covalently attached to a divalent nucleobase chosen from those listed in Table A, in which each instance of R1 is, independently, a protecting group or H and X is CH or N. In one example, the nucleobase is one of JB1, JB2, JB3 or JB4. In another embodiment, R1 is a protecting group, such as, for example and without limitation, a protecting group is chosen from one or more of methyl, formyl, ethyl, acetyl, anisyl, benzyl, benzoyl, carbamate, trifluoroacetyl, diphenylmethyl, triphenylmethyl, N-hydroxysuccinimide, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethozybenzyl, p-methoxyphenyl, 4-toluenesulfonyl, p-nitrobenzenesulfonates, 9-fluorenylmethyloxycarbonyl, 2-nitrophenylsulfenyl, 2,2,5,7,8-pentamethyl-chroman-6-sulfonyl, and p-bromobenzenesulfonyl. In one embodiment, the monomer is a peptide nucleic acid (PNA) monomer, and in another, γPNA. In yet another embodiment, the backbone monomer is a PNA or γPNA that is PEGylated, with one or more PEG moieties of two to fifty (—O—CH$_2$—CH$_2$—) residues. In a further embodiment, the monomer is a γPNA monomer having the structure:

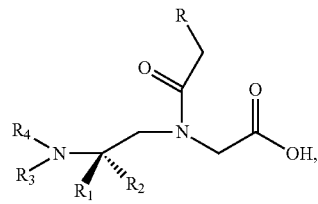

where R1, R2 and R4 are, independently, H, amino acid side chains, linear or branched (C$_1$-C$_8$)alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$) cycloalkyl, (C$_3$-C$_8$)aryl(C$_1$-C$_6$)alkylene, (C$_3$-C$_8$)cycloalkyl (C$_1$-C$_6$)alkylene, PEGylated moieties of the preceding comprising from 1 to 50 (—O—CH$_2$—CH$_2$—) residues, —CH$_2$—(OCH$_2$—CH$_2$)$_q$—OP$_1$, —CH$_2$—(OCH$_2$—CH$_2$)$_q$—NHP$_1$, —CH$_2$—(OCH$_2$—CH$_2$-0)$_q$—SP$_1$ and —CH$_2$—(SCH$_2$—CH$_2$)$_q$—SP$_1$, —CH$_2$—(OCH$_2$—CH$_2$)$_r$—OH, —CH$_2$—(OCH$_2$—CH$_2$)$_r$—NH$_2$, —CH$_2$—(OCH$_2$—CH$_2$)$_r$—NHC(NH)NH$_2$, or —CH$_2$—(OCH$_2$—CH$_2$)$_r$—S—S[CH$_2$CH$_2$]$_s$NHC(NH)NH$_2$, where P$_1$ is selected from the group consisting of H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl (C$_1$-C$_6$)alkylene and (C$_3$-C$_8$)cycloalkyl(C$_1$-C$_6$)alkylene; q is an integer from 0 to 10, inclusive; r and s are each independently integers from 1 to 50, inclusive; where R1 and R2 are different, and one of R1 or R2 is H, and R3 is H or a protecting group. In one non-limiting example, R2 is H, R1 is an amino acid side chain that is optionally PEGylated, with one or more PEG moieties of one to twelve (—O—CH$_2$—CH$_2$—) residues, and R3 is a protecting group.

In another embodiment, a divalent nucleobase is provided, chosen from the divalent nucleobases of Table A, in which each instance of R1 is, independently a protecting group or H and R is a reactive group. In another embodiment, the nucleobase is chosen from one the following:

JB1,
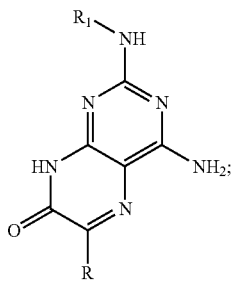
JB2,
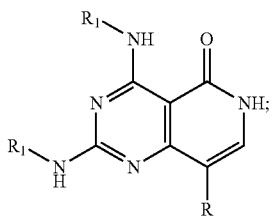
JB3,
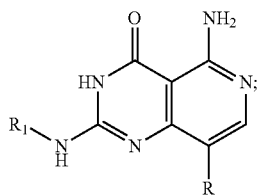
JB4,
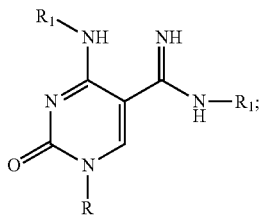
JB5,
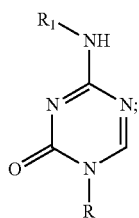
JB6,
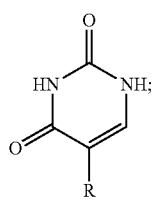
JB7,
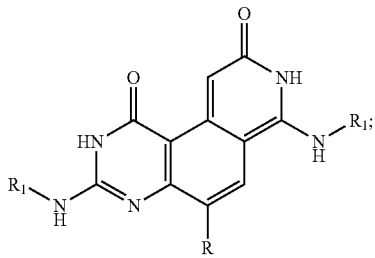
JB8,
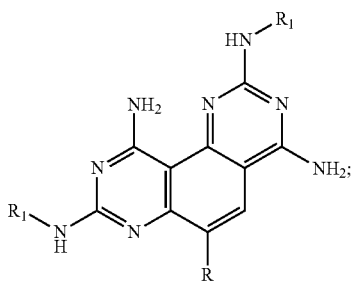
JB9,
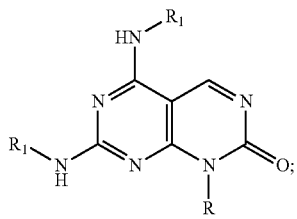
JB10,
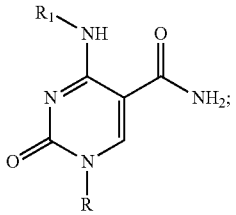
JB11,
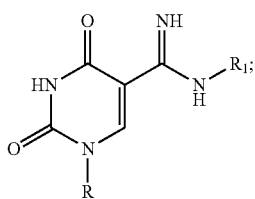
JB12,
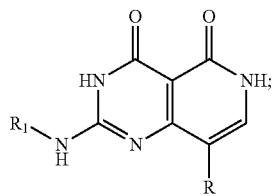

JB13,

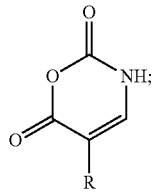

JB14,

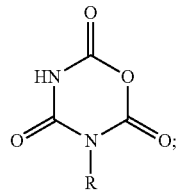

JB15,

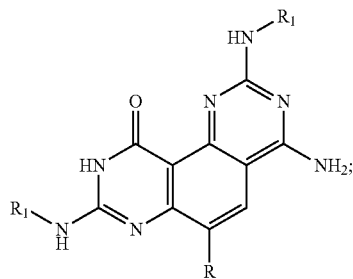

JB16,

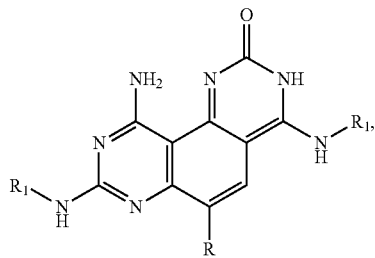

in which each instance of R1 is, independently a protecting group or H and R is carboxyl.

In another embodiment, a kit is provided comprising any monomer as described herein in a vessel. In one embodiment, the kit comprises monomers comprising each of JB1, JB2, JB3, JB4, JB5, JB6, JB7, JB8, JB9, JB9b, JB10, JB11, JB12, JB13, JB14, JB15, JB16 nucleobases, with each different monomer in a separate vessel. An array comprising a genetic recognition reagent as described herein also is provided.

A method of detection of a target sequence in a nucleic acid sample is provided. The method comprising contacting a genetic recognition reagent described herein with a sample comprising nucleic acid and detecting binding of the genetic recognition reagent with a nucleic acid.

Lastly, a method of isolation and purification or a nucleic acid containing a target sequence is provided. The method comprising, contacting a nucleic acid sample with a genetic recognition reagent as described herein, separating the nucleic acid sample from the genetic recognition reagent, leaving any nucleic acid bound to the genetic recognition reagent bound to the genetic recognition reagent, and separating the genetic recognition reagent from any nucleic acid bound to the genetic recognition reagent. In one embodiment of the method, the genetic recognition reagent is immobilized on a substrate. The method comprising contacting a nucleic acid with the substrate, washing the substrate to remove unbound nucleic acid from the substrate, but leaving bound nucleic acid bound to the substrate, and eluting the bound nucleic acid from the substrate.

DETAILED DESCRIPTION

Figure 1C:
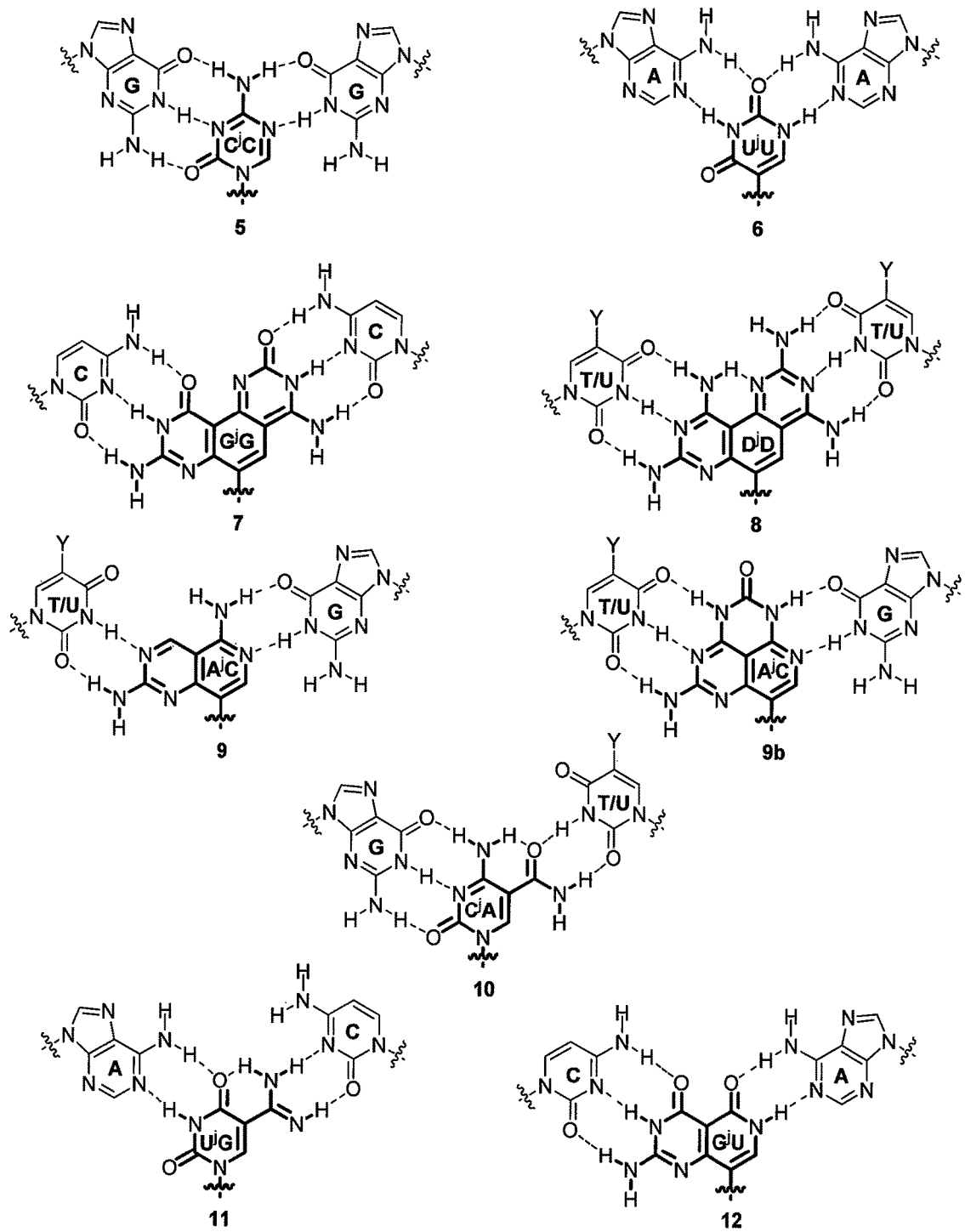
FIG. 1 illustrates hydrogen-bonding interactions between (A) natural base-pairs, (B) JB 1-4 (labeled 1-4) and the perfectly-matched DNA or RNA target and (C) JB 5-16 (labeled 5-16) and the mismatched DNA or RNA target.
Figure 1C:
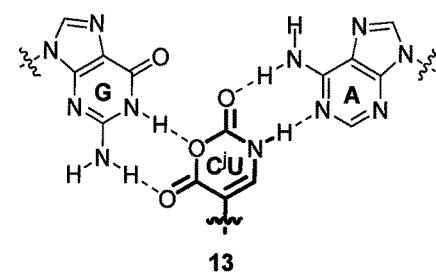
Figure 1C:
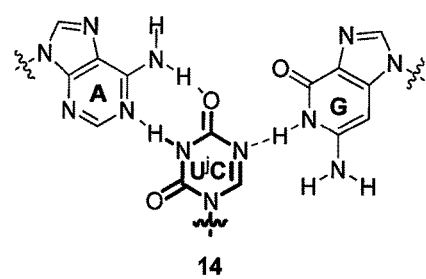
Figure 1C:
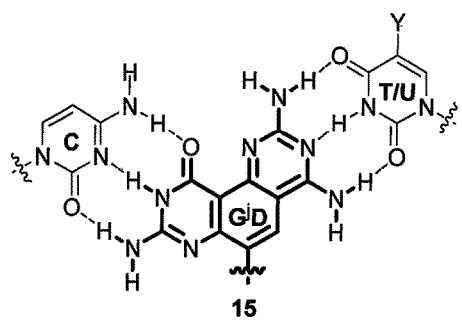
Figure 1C:
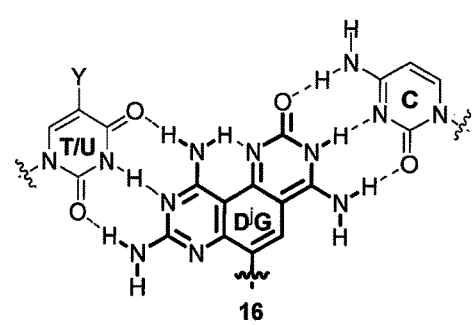

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

Provided herein are nucleic acids and analogs thereof, collectively "genetic recognition reagents" (genetic recognition reagent), that bind specifically to two nucleic acid strands, whether or not the two strands are independent strands, two portions of a single strand (e.g., in a hairpin) or contain mismatches in the sense that at one or more positions within the two strands at the site of binding to the genetic recognition reagents, the bases are not able to base pair according to traditional Watson-Crick base pairing (A-T/U, T/U-A, G-C or C-G). In one embodiment, the two strands binding the genetic recognition reagent are non-complementary, meaning they do not hybridize under physiological conditions and typically contain less than 50% complementarity, meaning that less than 50% of the bases in the two strands are mismatched when aligned to nucleobases of the genetic recognition reagent. Thus, depending upon choice of nucleobases in the sequence, the genetic recognition reagents described herein can invade or otherwise hybridize to two strands of fully-complementary, partially-complementary or non-complementary double-stranded nucleic acids.

In one embodiment, the genetic recognition reagents described herein comprise all divalent nucleobases. In another embodiment, the genetic recognition reagents described herein comprise at least one divalent nucleobases, with other nucleobases being monovalent. As used herein, a monovalent nucleobase binds one nucleobase on a single nucleic acid strand, while a divalent nucleobase, e.g., a Janus base described herein, binds to two nucleobases, one on a first nucleic acid strand, and another on a second nucleic acid strand.

Thus in one embodiment, divalent nucleobases are provided. Those nucleobases can be incorporated into a genetic recognition reagent monomer, which can then be incorporated into an oligomer of monomers with a desired sequence of nucleobases. Table A provides exemplary divalent "Janus" bases, their binding specificities (see also, FIG. 1), structures for the nucleobases, and structures for the nucleobases residue as it is attached to a nucleotide and/or a genetic recognition reagent. In the context of the present disclosure, a "nucleotide" refers to a monomer comprising at least nucleobases and a backbone element, which in a nucleic acid, such as RNA or DNA is ribose or deoxyribose. "Nucleotides" also typically comprise reactive groups that permit polymerization under specific conditions. In native DNA and RNA, those reactive groups are the 5' phosphate and 3' hydroxyl groups. For chemical synthesis of nucleic acids and analogs thereof, the bases and backbone monomers may contain modified groups, such as blocked amines, as are known in the art. A "nucleotide residue" refers to a single nucleotide that is incorporated into an oligonucleotide or polynucleotide. Likewise, a "nucleobases residue" refers to a nucleobases incorporated into a nucleotide or a nucleic acid or analog thereof. A "genetic recognition reagent" refers generically to a nucleic acid or a nucleic acid analog that comprises a sequence of nucleobases that is able to hybridize to a complementary nucleic acid sequence on a nucleic acid by cooperative base pairing, e.g., Watson-Crick base pairing or Watson-Crick-like base pairing. Of note, JB1-JB4 bind complementary bases (C-G, G-C, A-T and T-A), while JB5-JB16 bind mismatches, and thus can be used to bind two strands of matched and/or mismatched bases.

TABLE A

| | Divalent Nucleobases | | |
|---|---|---|---|
| Nucleobase | Bases represented | Nucleobase | Nucleobase residue |
| JB1 | T/D* | 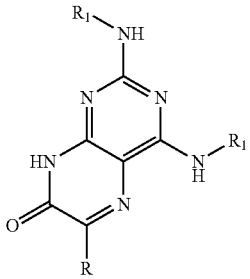 | 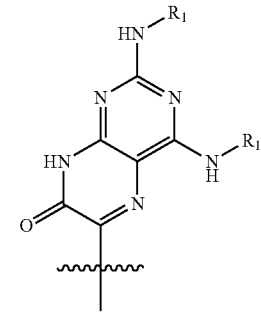 |
| JB2 | D/T | 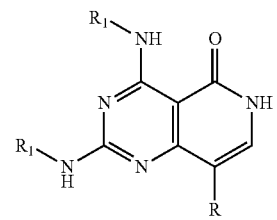 | 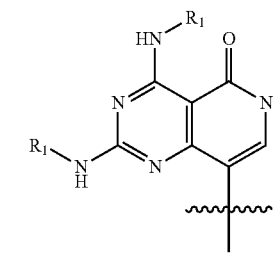 |
| JB3 | G/C | 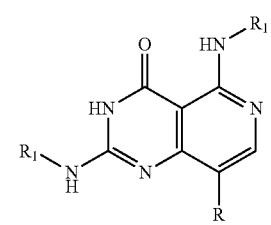 | 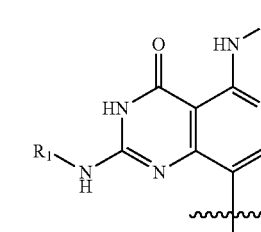 |

TABLE A-continued
Divalent Nucleobases
| Nucleobase | Bases represented | Nucleobase | Nucleobase residue |
|---|---|---|---|
| JB4 | C/G | 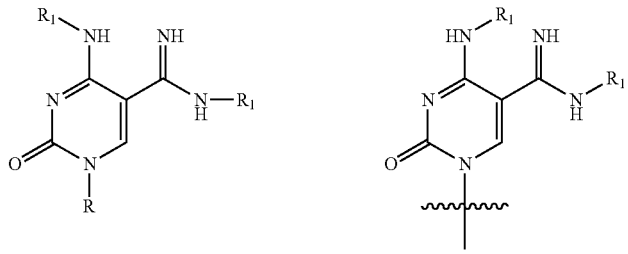 | |
| JB5 | C/C | 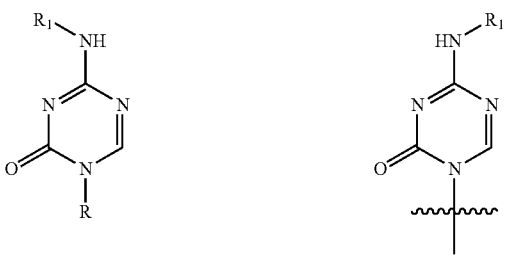 | |
| JB6 | U/U | 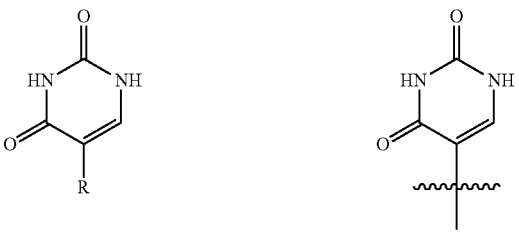 | |
| JB7 | G/G | 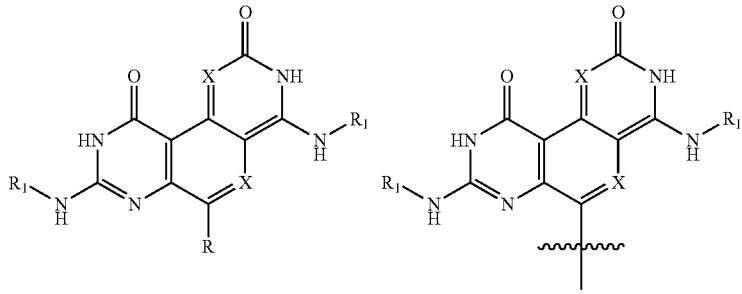 | |
| JB8 | D/D | 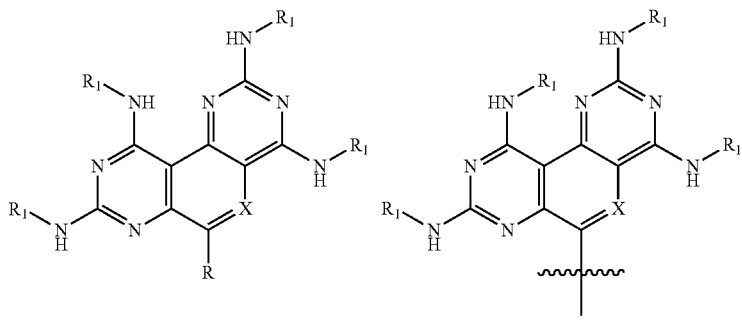 | |

TABLE A-continued
Divalent Nucleobases
| Nucleobase | Bases represented | Nucleobase | Nucleobase residue |
|---|---|---|---|
| JB9 | A/C | 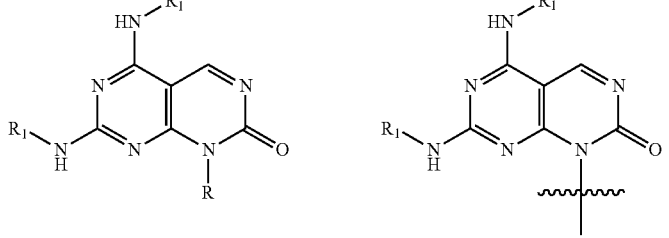 | |
| JB9b | A/C | 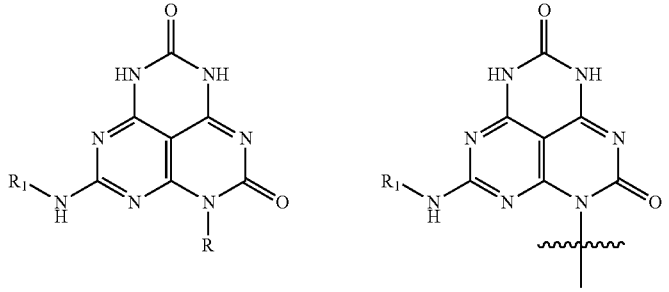 | |
| JB10 | C/A | 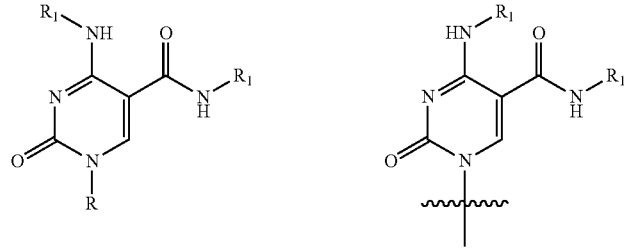 | |
| JB11 | U/G | 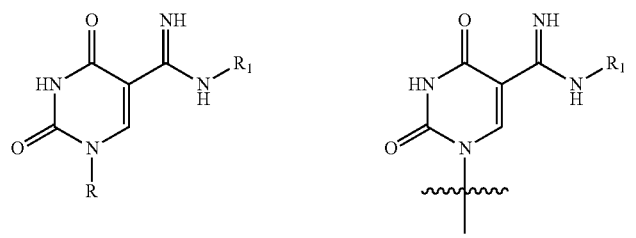 | |
| JB12 | G/U | 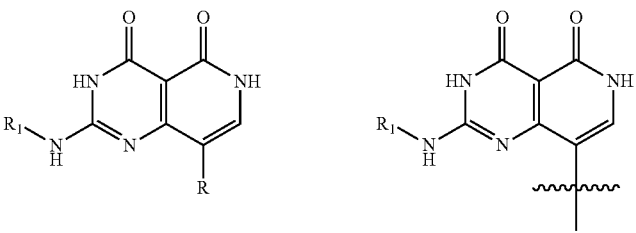 | |
| JB13 | C/U |  | |

TABLE A-continued

Divalent Nucleobases

| Nucleobase | Bases represented | Nucleobase | Nucleobase residue |
|---|---|---|---|
| JB14 | U/C | 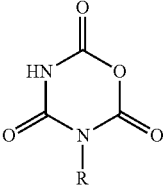 | 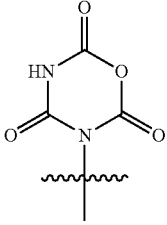 [SMILES: *n1c(=O)[nH]c(=O)oc1=O] |
| JB15 | G/D | 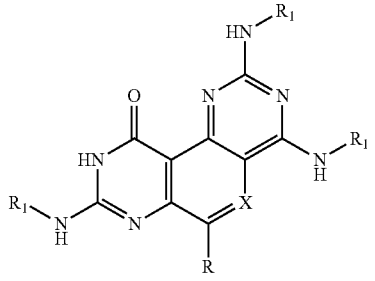 | 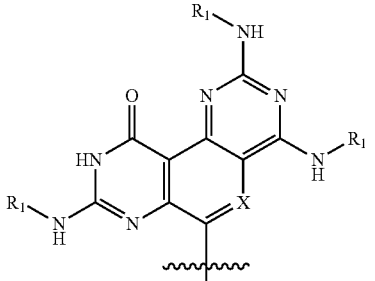 |
| JB16 | D/G | 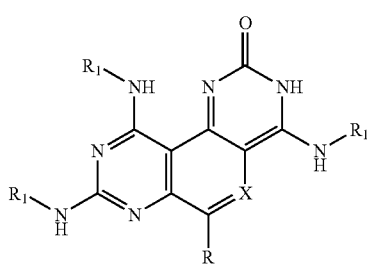 | 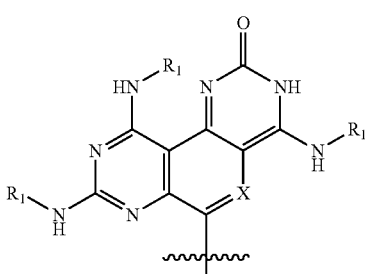 |

*diaminopurine, an adenine analog

In Table A, R is a reactive group that reacts with a backbone monomer during synthesis of a monomer. Non-limiting examples of a reactive group is a carboxyl (e.g., —C—C(O)OH), hydroxyl (e.g., —C—OH), cyanate (e.g., —C—C≡N), thiol (e.g., —C—SH), $(CH_2)_n CO_2 H$ or $(CH_2)_n CO_2 Y$ (n=1-5, Y=any leaving group such as Cl, alkyl, aryl, etc.). X is either CH or N. R1s are each, independently: H or a protecting group. In one embodiment, all instances of X are C(=CH—) and all instances are R1. Where all instances of R1 are H, the compounds or moieties are said to be deprotected. Depending on the chemistries employed to prepare the monomers or oligomers comprising the monomers, one or more of R1 is optionally protected using a protecting group, as is needed. Protecting groups for amines, include, for example and without limitation: methyl, formyl, ethyl, acetyl, anisyl, benzyl, benzoyl, carbamate, trifluoroacetyl, diphenylmethyl, triphenylmethyl, N-hydroxysuccinimide, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethoxybenzyl, p-methoxyphenyl, 4-toluenesulfonyl, p-nitrobenzenesulfonates, 9-fluorenylmethyloxycarbonyl, 2-nitrophenylsulfenyl, 2,2,5,7,8-pentamethyl-chroman-6-sulfonyl, and p-bromobenzenesulfonyl. JB9b is a structural variation of JB9.

The structure,

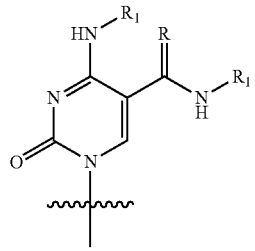

is generic to JB4 and JB10, wherein R is

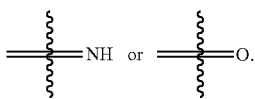

The structure,

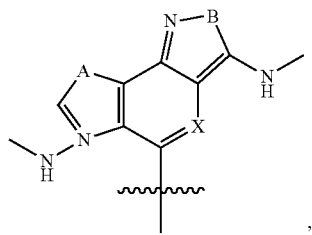

is generic to JB8, JB15 and JB 16, where:
A is

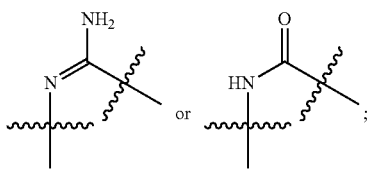 [SMILES: */N=C(\*)N ; *NC(*)=O]

and B is

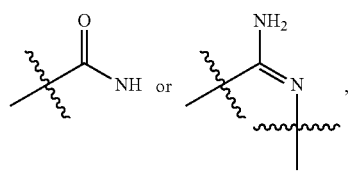

where either A is

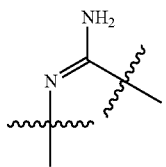 [SMILES: */N=C(\*)N]

or B is

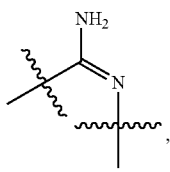 [SMILES: */N=C(\*)N]

and X is CH or N.

The nucleobases of Table A have divalent binding affinity, as indicated. FIG. 1 depicts the hydrogen bonding of the sixteen divalent nucleobases of Table A, while comparing to Watson-Crick-like hydrogen-bonding interactions with natural bases. Of note, JB1, JB2, JB3 and JB4 account for matched (complementary) sequences, while the remainder of the compounds bind all other iterations of mis-matched sequences.

Figure 2:
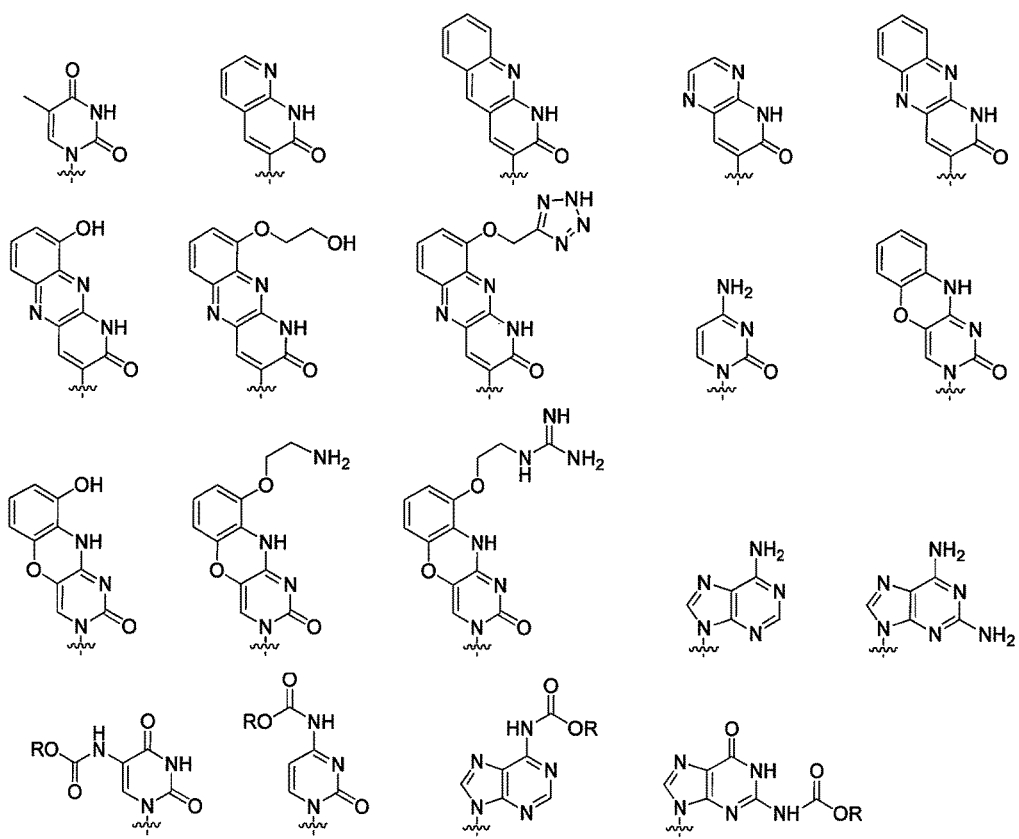
FIG. 2 provides structures of exemplary nucleobases.

Nucleobases are recognition moieties that bind specifically to one or more of adenine, guanine, thymine, cytosine, and uracil, e.g., by Watson-Crick or Watson-Crick-like base pairing by hydrogen bonding. A "nucleobase" includes primary nucleobases: adenine, guanine, thymine, cytosine, and uracil, as well as modified purine and pyrimidine bases, such as, without limitation, hypoxanthine, xanthene, 7-methylguanine, 5, 6, dihydrouracil, 5-methylcytosine, and 5-hydroxymethylcytosine. FIG. 2 also depicts non-limiting examples of nucleobases, including monovalent nucleobases (e.g., adenine, cytosine, guanine, thymine or uracil, which bind to one strand of nucleic acid or nucleic acid analogs), and "clamp" nucleobases, such as a "G-clamp," which binds complementary nucleobases with enhanced strength. Additional purine, purine-like, pyrimidine and pyrimidine-like nucleobases are known in the art, for example as disclosed in U.S. Pat. Nos. 8,053,212, 8,389,703, and 8,653,254.

Also provided herein are nucleotides having the structure A-B wherein A is a backbone monomer and B is a divalent nucleobase as described above. The backbone monomer can be any suitable nucleic acid backbone monomer, such as a ribose triphosphate or deoxyribose triphosphate, or a monomer of a nucleic acid analog, such as peptide nucleic acid (PNA), such as a gamma PNA (γPNA). The backbone monomer includes both the structural "residue" component, such as the ribose in RNA, and any active groups that are modified in linking monomers together, such as the 5' triphosphate and 3' hydroxyl groups of a ribonucleotide, which are modified when polymerized into RNA to leave a phosphodiester linkage. Likewise for PNA, the C-terminal carboxyl and N-terminal amine active groups of the N-(2-aminoethyl)glycine backbone monomer are condensed during polymerization to leave a peptide (amide) bond. In another embodiment, the active groups are phosphoramidite groups useful for phosphoramidite oligomer synthesis, as is broadly-known in the arts. The nucleotide also optionally comprises one or more protecting groups as are known in the art, such as 4,4'-dimethoxytrityl (DMT), and as described herein. A number of additional methods of preparing synthetic genetic recognition reagents are known, and depend on the backbone structure and particular chemistry of the base addition process. Determination of which active groups to utilize in joining nucleotide monomers and which groups to protect in the bases, and the required steps in preparation of oligomers is well within the abilities of those of ordinary skill in the chemical arts and in the particular field of nucleic acid and nucleic acid analog oligomer synthesis.

Figure 3:
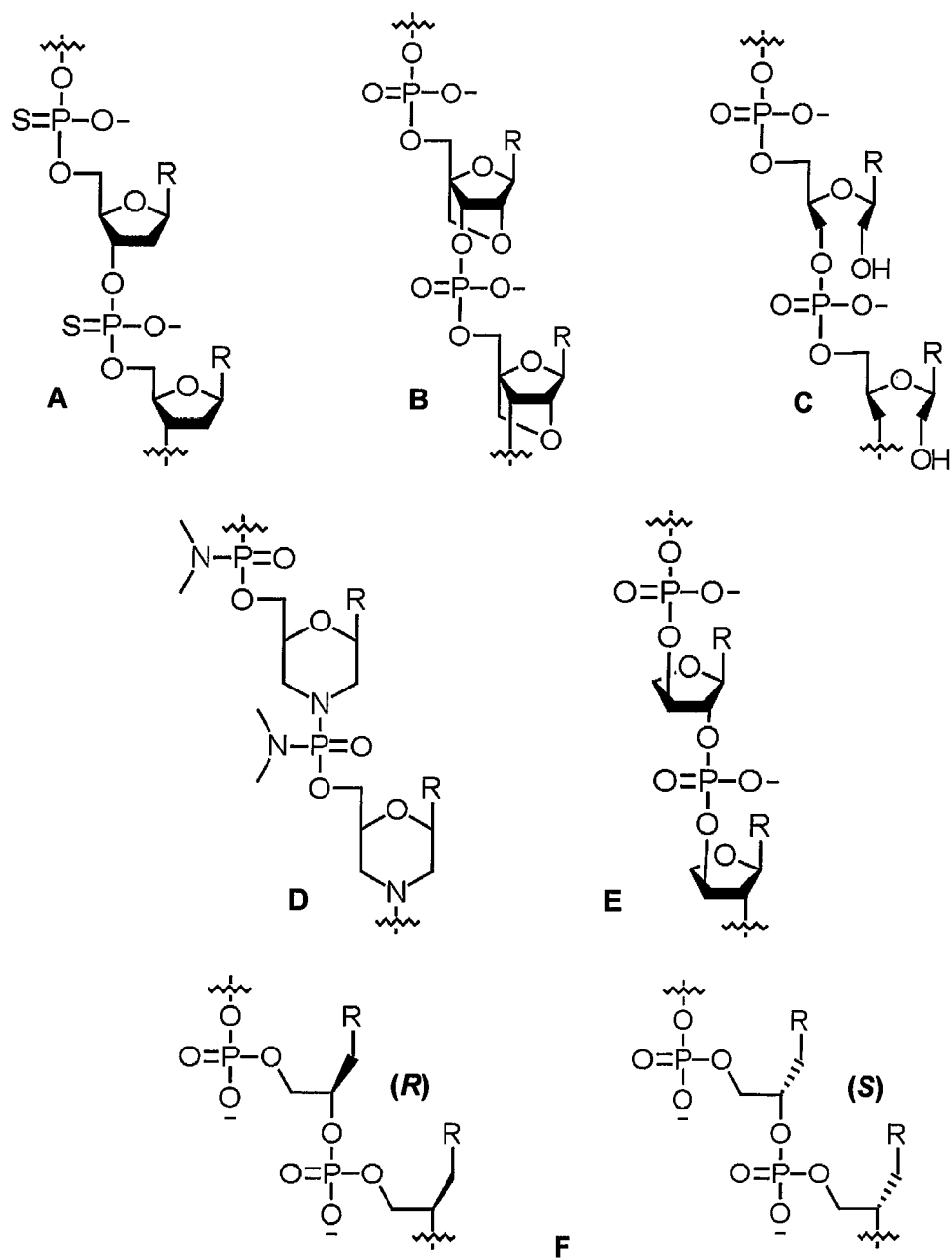
FIGS. 3A-3F provide exemplary structures for nucleic acid analogs.

Non-limiting examples of common nucleic acid analogs include peptide nucleic acids, such as γPNA, phosphorothioate (e.g., FIG. 3A), locked nucleic acid (2'-O-4'-C-methylene bridge, including oxy, thio or amino versions thereof, e.g., FIG. 3B), unlocked nucleic acid (the C2'-C3' bond is cleaved, e.g., FIG. 3C), 2'-O-methyl-substituted RNA, morpholino nucleic acid (e.g., Fig_D), threose nucleic acid (e.g., FIG. 3E), glycol nucleic acid (e.g., FIG. 3F, showing R and S Forms), etc. FIG. 3A-F shows monomer structures for various examples of nucleic acid analogs. FIGS. 3A-3F each show two monomer residues incorporated into a longer chain as indicated by the wavy lines. Incorporated monomers are referred to herein as "residues" and the part of the nucleic acid or nucleic acid analog oligomer or polymer excluding the nucleobases is referred to as the "backbone" of the nucleic acid or nucleic acid analog. As an example, for RNA, an exemplary nucleobase is adenine, a corresponding monomer is adenosine triphosphate, and the incorporated residue is an adenosine monophosphate residue. For RNA, the "backbone" consists of ribose subunits linked by phosphates, and thus the backbone monomer is ribose triphosphate prior to incorporation and a ribose monophosphate residue after incorporation.

According to one embodiment, with the advent of conformationally-preorganized γPNA, precise sequence selection is no longer an issue (Bahal, R., et al. "Sequence-unrestricted, Watson-Crick recognition of double helical B-DNA by (R)-MiniPEG-γPNAs (2012) *ChemBioChem* 13:56-60). γPNA can be designed to bind to any sequence of double helical B-DNA based on the well-established rules of Watson-Crick base-pairing. However, with an arsenal of only natural nucleobases as recognition elements, strand invasion of DNA by γPNA is confined to sub-physiological ionic strengths (Rapireddy, S., R. et al. "Strand invasion of mixed-sequence, double-helical B-DNA by γ-peptide nucleic acids containing G-clamp nucleobases under physiological conditions," (2011) *Biochemistry* 50:3913-3918). A reduction in the efficiency of productive γPNA binding at elevated ionic strengths is not due to the lack of base-pair accessibility, but rather due to the lack of binding free energy. Under physiological conditions, DNA double helix is sufficiently dynamic to permit strand invasion, provided that the required binding free energy could be met. One way to improve the binding free energy of such a system would be to enhance the base-stacking and H-bonding capabilities of the recognition elements, which is met by the present invention. In one embodiment, γPNA monomers and oligomers containing a specialized set of divalent "Janus'" nucleobases (JBs) that are capable of forming directional hydrogen bonding interactions with both strands of the DNA or RNA double helix is performed. Examples of the chemical structures of the JBs are illustrated in Table A. Non-limiting examples of γPNA monomers and oligomers are provided below, with, e.g., an amino acid side chain, or a PEGylated (polyethyleneglycol, or PEG) group at the chiral gamma carbon.

As used herein, the term "nucleic acid" refers to deoxyribonucleic acids (DNA) and ribonucleic acids (RNA). Nucleic acid analogs include, for example and without limitation: 2'-O-methyl-substituted RNA, locked nucleic acids, unlocked nucleic acids, triazole-linked DNA, peptide nucleic acids, morpholino oligomers, dideoxynucleotide oligomers, glycol nucleic acids, threose nucleic acids and combinations thereof including, optionally ribonucleotide or deoxyribonucleotide residue(s). Herein, "nucleic acid" and "oligonucleotide", which is a short, single-stranded structure made of up nucleotides, are used interchangeably. An oligonucleotide may be referred to by the length (i.e. number of nucleotides) of the strand, through the nomenclature "-mer". For example, an oligonucleotide of 22 nucleotides would be referred to as a 22-mer.

A "peptide nucleic acid" refers to a DNA or RNA analog or mimic in which the sugar phosphodiester backbone of the DNA or RNA is replaced by a N-(2-aminoethyl)glycine unit. A gamma PNA (γPNA) is an oligomer or polymer of gamma-modified N-(2-aminoethyl)glycine monomers of the following structure:

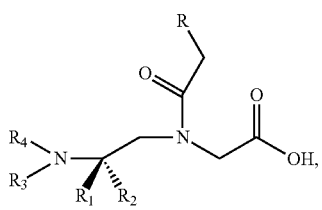

where at least one of R1 or R2 attached to the gamma carbon is not a hydrogen, or R1 and R2 are different, such that the gamma carbon is a chiral center. When R1 and R2 are hydrogen (N-(2-aminoethyl)-glycine backbone), or the same, there is no such chirality about the gamma carbon. When R1 and R2 are different, such as when one of R1 or R2 are H and the other is not, there is chirality about the gamma carbon. Typically, for γPNAs and γPNA monomers, either of R1 or R2 is an H and the other is an amino acid sidechain or an organic group, such as a ($C_1$-$C_{10}$) organic group or hydrocarbon, optionally PEGylated with from 1 to 50 oxyethylene residues—that is, $[-O-CH_2-CH_2-]_n$, where n is 1 to 50, inclusive. R4 can be H or an organic group, such as a ($C_1$-$C_{10}$) organic group or hydrocarbon, optionally PEGylated with from 1 to 50 oxyethylene residues. For example and without limitation, R1, R2 and R4 are, independently, H, amino acid side chains, linear or branched ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, PEGylated moieties of the preceding comprising from 1 to 50 ($-O-CH_2-CH_2-$) residues, $-CH_2-(OCH_2-CH_2)_q OP_1$, $-CH_2-(OCH_2-CH_2)_q-NHP_1$, $-CH_2-(OCH_2-CH_2-O)_q-SP_1$ and $-CH_2-(SCH_2-CH_2)_q-SP_1$, $-CH_2-(OCH_2-CH_2)_r-OH$, $-CH_2-(OCH_2-CH_2)_r-NH_2$, $-CH_2-(OCH_2-CH_2)_r-NHC(NH)NH_2$, or $-CH_2-(OCH_2-CH_2)_r-S-S[CH_2CH_2]_sNHC(NH)NH_2$, where $P_1$ is selected from the group consisting of H, ($C_1$-$C_8$)alkyl, ($C_2$-$C_8$)alkenyl, ($C_2$-$C_8$)alkynyl, ($C_3$-$C_8$)aryl, ($C_3$-$C_8$)cycloalkyl, ($C_3$-$C_8$)aryl($C_1$-$C_6$)alkylene and ($C_3$-$C_8$)cycloalkyl($C_1$-$C_6$)alkylene; q is an integer from 0 to 10, inclusive; r and s are each independently integers from 1 to 50, inclusive; where R1 and R2 are different, and optionally one of R1 or R2 is H. R3 is H or a protective group A γPNA monomer incorporated into a γPNA oligomer or polymer,

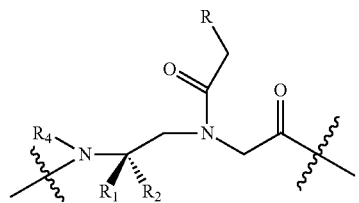

is referred to herein as a "γPNA monomer residue", with each residue having the same or different R group as its nucleobase, such as adenine, guanine, cytosine, thymine and uracil bases, or other nucleobases, such as the monovalent and divalent bases described herein, such that the order of bases on the γPNA is its "sequence", as with DNA or RNA. The depicted γPNA monomer and residue structures show a backbone monomer, and a backbone monomer residue, respectively, attached to a nucleobase (R). A sequence of nucleobases in a nucleic acid or a nucleic acid analog oligomer or polymer, such as a γPNA oligomer or polymer, binds to a complementary sequence of adenine, guanine, cytosine, thymine and/or uracil residues in a nucleic acid strand by cooperative bonding, essentially as with Watson-Crick binding of complementary bases in double-stranded DNA or RNA. "Watson-Crick-like" bonding refers to hydrogen bonding of nucleobases other than G, A, T, C or U, such as the bonding of the divalent bases shown herein with G, A, T, C, U or other nucleobases.

Figure 4:
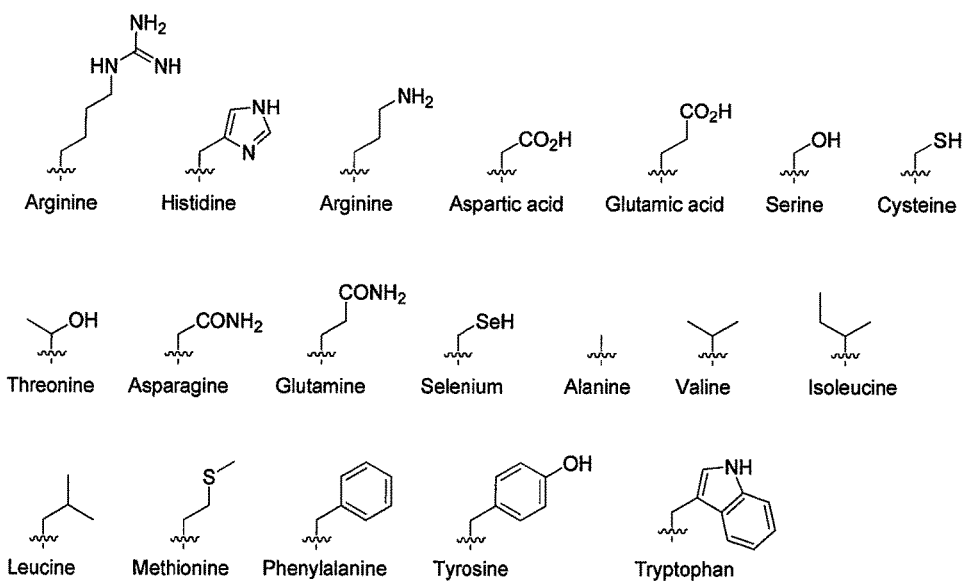
FIG. 4 provides examples of amino acid side chains.

An "amino acid side chain" is a side chain for an amino acid. Amino acids have the structure:

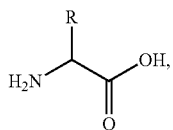

where R is the amino acid side chain. Non-limiting examples of amino acid side chains are shown in FIG. 4. Glycine is not represented because in the embodiment R1s are both H.

The following are exemplary definitions of various moieties or groups as used herein. "Alkyl" refers to straight, branched chain, or cyclic hydrocarbon groups including from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached to any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, ethylene (—CH$_2$—CH$_2$—). "Optionally substituted alkylene" refers to alkylene or substituted alkylene.

"Alkene or alkenyl" refers to straight, branched chain, or cyclic hydrocarbyl groups including from 2 to about 20 carbon atoms, such as, without limitation $C_{1-3}$, $C_{1-6}$, $C_{1-10}$ groups having one or more, e.g., 1, 2, 3, 4, or 5, carbon-to-carbon double bonds. "Substituted alkene" refers to alkene substituted at 1 or more, e.g., 1, 2, 3, 4, or 5 positions, which substituents are attached at any available atom to produce a stable compound, with substitution as described herein. "Optionally substituted alkene" refers to alkene or substituted alkene. Likewise, "alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne or alkynyl" refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below. The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a ($C_1$-$C_6$)alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a ($C_1$-$C_{10}$)alkyl group wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof. The term "ether" or "oxygen ether" refers to ($C_1$-$C_{10}$)alkyl group wherein one or more of the alkyl group's carbon atoms is replaced with an —O— group. The term ether includes —CH$_2$—(OCH$_2$—CH$_2$)$_q$OP$_1$ compounds where $P_1$ is a protecting group, —H, or a ($C_1$-$C_{10}$)alkyl. Exemplary ethers include polyethylene glycol, diethylether, methylhexyl ether and the like.

The term "thioether" refers to ($C_1$-$C_{10}$)alkyl group wherein one or more of the alkyl group's carbon atoms is replaced with an —S— group. The term thioether includes —CH$_2$—(SCH$_2$—CH$_2$)$_q$—SP$_1$ compounds where $P_1$ is a protecting group, —H, or a ($C_1$-$C_{10}$)alkyl. Exemplary thioethers include dimethylthioether, ethylmethyl thioether. Protecting groups are known in the art and include, without limitation: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), dimethoxytrityl (DMT), 1-(4,4-dimethyl-2,6-dioxacyclohexylidene)ethyl (Dde), diathiasuccinoyl (Dts), benzothiazole-2-sulfonyl (Bts) and monomethoxytrityl (MMT) groups.

"Aryl," alone or in combination refers to an aromatic monocyclic or bicyclic ring system such as phenyl or naphthyl. "Aryl" also includes aromatic ring systems that are optionally fused with a cycloalkyl ring. A "substituted aryl" is an aryl that is independently substituted with one or more substituents attached at any available atom to produce a stable compound, wherein the substituents are as described herein. "Optionally substituted aryl" refers to aryl or substituted aryl. "Arylene" denotes divalent aryl, and "substituted arylene" refers to divalent substituted aryl. "Optionally substituted arylene" refers to arylene or substituted arylene.

"Heteroatom" refers to N, O, P and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with N, O, P or S.

"Cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below. "Cycloalkylene" refers to divalent cycloalkyl. The term "optionally substituted cycloalkylene" refers to cycloalkylene that is substituted with 1, 2 or 3 substituents, attached at any available atom to produce a stable compound, wherein the substituents are as described herein.

"Carboxyl" or "carboxylic" refers to group having the indicated number of carbon atoms and terminating in a —C(O)OH group, thus having the structure —R—C(O)OH, where R is a divalent organic group that includes linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc.

"$(C_3-C_8)$aryl-$(C_1-C_6)$alkylene" refers to a divalent alkylene wherein one or more hydrogen atoms in the $C_1-C_6$ alkylene group is replaced by a $(C_3-C_8)$aryl group. Examples of $(C_3-C_8)$aryl-$(C_1-C_6)$alkylene groups include without limitation 1-phenylbutylene, phenyl-2-butylene, 1-phenyl-2-methylpropylene, phenylmethylene, phenylpropylene, and naphthylethylene. The term "$(C_3-C_8)$cycloalkyl-$(C_1-C_6)$alkylene" refers to a divalent alkylene wherein one or more hydrogen atoms in the $C_1-C_6$ alkylene group is replaced by a $(C_3-C_8)$cycloalkyl group. Examples of $(C_3-C_8)$cycloalkyl-$(C_1-C_6)$alkylene groups include without limitation 1-cycloproylbutylene, cyproyl-2-butylene, cyclopentyl-1-phenyl-2-methylpropylene, cyclobutyhnethylene and cyclohexylpropylene.

Unless otherwise indicated, the nucleic acids and nucleic acid analogs described herein are not described with respect to any particular sequence of bases. The present disclosure is directed to divalent nucleobases, compositions comprising the divalent nucleobases, and methods of use of the divalent nucleobases and compounds containing those nucleobases, and the usefulness of any specific embodiments described herein, while depending upon a specific sequence in each instance, is generically applicable. Based on the abundance of published work with nucleic acids, nucleic acid analogs and PNA (e.g., γPNA), it is expected that any nucleobase sequence attached to the backbone of the described γPNA oligomers would hybridize in an expected, specific manner with a complementary nucleobase sequence of a target nucleic acid or nucleic acid analog by Watson-Crick or Watson-Crick-like hydrogen bonding. One of ordinary skill would understand that the compositions and methods described herein are sequence-independent and describe novel, generalized compositions comprising divalent nucleobases and related methods.

In another embodiment, a genetic recognition reagent oligomer is provided, comprising at least one divalent nucleobase. The genetic recognition reagent comprises a backbone and at least two nucleobases, at least one of which is a divalent nucleobase as described herein. This structure is shown schematically in Formula 3:

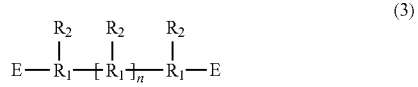

(3)

where R1 is a backbone monomer residue and R2s are, independently nucleobases, where at least one instance of R2 is a divalent nucleobase, such as any one of JB1-JB16 as shown herein. E are independently end (terminal) groups that are part of the terminal monomer residues, and "n" is any positive integer or 0, for example 48 or less, 28 or less, 23 or less, and 18 or less, including 0, 1, 2, 3, 4, 5, 6, 7, 8, 9, 10, 11, 12, 13, 14, 15, 16, 17, and 18. Typically, all instances of R1 are the same with the exception of the terminal monomer residues which typically have different end-groups E as compared to internal monomers, such as, without limitation $NH_2$ and $C(O)OH$ or $CONH_2$ at the respective N-terminal and C-terminal ends for PNAs, and hydroxyl groups at the 5' and 3' ends of nucleic acids.

In one embodiment of the present invention, the genetic recognition reagents are implemented on an array. Arrays are particularly useful in implementing high-throughput assays, such as genetic detection assays. As used herein, the term "array" refers to reagents, for example the genetic recognition reagents described herein, located at two or more discrete, identifiable and/or addressable locations on a substrate. In one embodiment, an array is an apparatus having two or more discrete, identifiable reaction chambers, such as, without limitation a 96-well dish, in which reactions comprising identified constituents are performed. In an exemplary embodiment, two or more genetic recognition reagents described herein are immobilized onto a substrate in a spatially addressable manner so that each individual primer or probe is located at a different and (addressable) identifiable location on the substrate. Substrates include, without limitation, multi-well plates, silicon chips and beads. In one embodiment, the array comprises two or more sets of beads, with each bead set having an identifiable marker, such as a quantum dot or fluorescent tag, so that the beads are individually identifiable using, for example and without limitation, a flow cytometer. In one embodiment, an array is a multi-well plate containing two or more wells with the descried genetic recognition reagents for binding specific sequences. As such, reagents, such as probes and primers may be bound or otherwise deposited onto or into specific locations on an array. Reagents may be in any suitable form, including, without limitation: in solution, dried, lyophilized or glassified. When linked covalently to a substrate, such as an agarose bead or silicon chip, a variety of linking technologies are known for attaching chemical moieties, such as the genetic recognition reagents to such substrates. Linkers and spacers for use in linking nucleic acids, peptide nucleic acids and other nucleic acid analogs are broadly known in the chemical and array arts and for that reason are not described herein. As a non-limiting example, a γPNA genetic recognition reagent contains a reactive amine, which can be reacted with carboxyl, cyanogen bromide-, N-hydroxysuccinimide ester-, carbonyldiimidazole- or aldehyde-functional agarose beads, available, for instance from Thermo Fisher Scientific (Pierce Protein Biology Products), Rockford, Ill. and a variety of other sources. The genetic recognition reagents described herein can be attached to a substrate in any manner, with or without linkers. Informatics and/or statistical software or other computer-implemented processes for analyzing array data and/or identifying genetic risk factors from data obtained from a patient sample, are known in the art.

Certain of the JB divalent compositions are expected to exhibit fluorescence, such as JB1, JB2 and JB3, due to their ring structure. These compositions can, of course, be used as fluorochromes, or the intrinsic fluorescence can be employed as a probe, for example, by binding target sequences in an in situ assay or in a gel or blot, such that a target sequence can be visualized.

Thus, according to one embodiment of the present invention, a method is provided for detection of a target sequence in a nucleic acid, comprising contacting a genetic recognition reagent composition as described herein with a sample comprising nucleic acid and detecting binding of the genetic recognition reagent with a nucleic acid. In one embodiment, the genetic recognition reagent is immobilized on a substrate, for example in an array, and labeled (e.g., fluorescently labeled or radiolabeled) nucleic acid sample is contacted with the immobilized genetic recognition reagent and the amount of labeled nucleic acid specifically bound to the genetic recognition reagent is measured. In a variation, genetic recognition reagent or a nucleic acid comprising a target sequence of the genetic recognition reagent is bound to a substrate, and a labeled nucleic acid comprising a target sequence of the genetic recognition reagent or a labeled genetic recognition reagent is bound to the immobilized genetic recognition reagent or nucleic acid, respectively to form a complex. In one embodiment, the nucleic acid of the complex comprises a partial target sequence so that a nucleic acid comprising the full target sequence would out-compete the complexed nucleic acid for the genetic recognition reagent. The complex is then exposed to a nucleic acid sample and loss of bound label from the complex could be detected and quantified according to standard methods, facilitating quantification of a nucleic acid marker in the nucleic acid sample. These are merely two of a large number of possible analytical assays that can be used to detect or quantify the presence of a specific nucleic acid in a nucleic acid sample.

By "immobilized" in reference to a composition such as a nucleic acid or genetic recognition reagent as described herein, it is meant attached to a substrate of any physical structure or chemical composition. The immobilized composition is immobilized by any method useful in the context of the end use. The composition is immobilized by covalent or non-covalent methods, such as by covalent linkage of amine groups to a linker or spacer, or by non-covalent bonding, including Van derWaals and/or hydrogen bonding. A "label" is a chemical moiety that is useful in detection of, or purification or a molecule or composition comprising the label. A label may be, for example and without limitation, a radioactive moiety, such as $^{14}C$, $^{32}P$, $^{35}S$, a fluorescent dye, such as fluorescein isothiocyanate or a cyanine dye, an enzyme, or a ligand for binding other compounds such as biotin for binding streptavidin, or an epitope for binding an antibody. A multitude of such labels, and methods of use thereof are known to those of ordinary skill in the immunology and molecular biology arts.

In yet another embodiment of the present invention, a method of isolation and purification or a nucleic acid containing a target sequence is provided. In one non-limiting embodiment, a genetic recognition reagent as described herein is immobilized on a substrate, such as a bead (for example and without limitation, an agarose bead, a bead containing a fluorescent marker for sorting, or a magnetic bead), porous matrix, surface, tube, etc. A nucleic acid sample is contacted with the immobilized genetic recognition reagent and nucleic acids containing the target sequence bind to the genetic recognition reagent. The bound nucleic acid is then washed to remove unbound nucleic acids, and the bound nucleic acid is then eluted, and can be precipitated or otherwise concentrated by any useful method as are broadly known in the molecular biological arts.

In a further embodiment, kits are provided. A kit comprises at a minimum a vessel of any form, including cartridges for automated PNA synthesis, which may comprise one or more vessels in the form of compartments. Vessels may be single-use, or contain sufficient contents for multiple uses. A kit also may comprise an array. A kit may optionally comprise one or more additional reagents for use in making or using genetic recognition reagents in any embodiment described herein. The kit comprises a vessel containing any divalent nucleobase described herein, or monomers or genetic recognition reagents according to any embodiment described herein. Different nucleobases, monomers or genetic recognition reagents are typically packages into separate vessels, which may be separate compartments in a cartridge.

EXAMPLES

The examples described herein illustrate advantages of the disclosed technology over traditional oligonucleotide systems. γPNA containing JB1-4 as recognition elements (γPNAJB1-4) can be designed to bind to any sequence of double-stranded DNA (dsDNA) or RNA (dsRNA) under physiological conditions through direct hydrogen bonding interactions. These probes typically are as short 3 nt in length and as long as 25 nt in length. The shorter probes, 10 nt or less, are especially easier to synthesize and scale up, via solution—as opposed to solid-phase chemistry, and are more readily taken up by cells.

Recognition of dsDNA or dsRNA by γPNAJB1-4 is more sequence-specific than the existing antigene or antisense platforms because a mismatch on one face of JB would result in a mismatch on the second face. Binding of γPNAJB1-4 to DNA or RNA is more selective for double-strand than for single-strand or primary (unstructured) sequences. Additionally, γPNA containing JB 1-16 (γPNAJB1-16) can be designed to bind to any secondary or tertiary structure of RNA and modulate its folding patterns and three-dimensional architectures.

Furthermore, these examples also provide distinctive features and advantages over small-molecule drugs or other ligands. Recognition of the γPNAJB probes occurs in a sequence-specific and predictable manner in accordance with the Watson-Crick and Janus base-pairing rules. Because they are modular in nature, γPNAJB probes could be modified to match the sequence of any RNA. This is an essential requirement for countering drug resistance due to emergence of genetic mutations—in particular, for genetic targets, such as that of cancer, bacteria, viral and parasite genomes or transcriptomes.

Example applications include, but are not limited to, reagents for detection, analysis and purification of DNA and RNA molecules, and for molecular tools for regulating gene expression, correcting genetic mutations, modulating RNA splicing, controlling microRNA functions, and modulation of RNA folding patterns and architectures. These applications will positively contribute to diagnostics; for example to detect DNA and RNA sequence and structural variations. Additionally this platform will advance medicine; as an example for use as therapeutics for treating a variety of genetic diseases associated with misregulation of gene expression including cancer, deregulation of RNA splicing, DNA and RNA unstable repeats, and fungal, bacterial and viral biology and infections.

The applications of this nucleic acid platform using γPNA and the Janus nucleobases span basic research in biology and biotechnology, diagnostics, and therapeutics. This platform, which targets double-stranded DNA and RNA has been demonstrated and described in accordance with several examples, which are intended to be illustrative in all aspects rather than restrictive. Thus, the present invention is capable of many variations in detailed implementation, which may be derived from the description contained herein by a person of ordinary skill in the art.

Example 1

Computer Simulation of Interactions of γPNA with DNA and RNA

DNA binding properties of γPNA include efficiencies from backbone preorganization (as defined by the stereochemistry at the γ-position, which determines the helical sense of the oligomer) and improvements in hydrogen-bonding and base-stacking capabilities. Divalent nucleobases JB 1-4, were designed to bind to the perfectly matched, and JB 5-16 were designed to bind to mismatched base-pairs in the DNA or RNA double helix. In both cases binding occurs via strand invasion, whereby one face of the divalent nucleobase forms Watson-Crick-like hydrogen-bonding interactions with natural bases on one strand of DNA or RNA double helix, while a second face forms 'Janus' hydrogen-bonding interactions with the complementary strand of the DNA or RNA target. As indicated above, FIG. 1 illustrates these hydrogen-bonding interactions, while comparing to Watson-Crick-like hydrogen-bonding interactions with natural bases.

In one embodiment, the overall geometry, bond distance, and chemical functionalities of these divalent "Janus" nucleobases are carefully crafted so that they can be used interchangeably to target the perfectly-matched as well as mismatched binding sites, or a combination thereof. It is demonstrated from these examples that this platform of γPNA monomers/oligomers containing the JBs are more selective for double-stranded DNA or RNA, in addition to recognizing secondary and tertiary structures. DNA-γPNA interactions were modeled by computer simulation using AMBER10 (University of California, San Francisco, Calif.). The γPNA is based on alanine, having the monomer structure

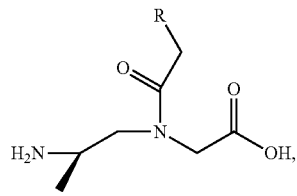

and thus having the residue structure

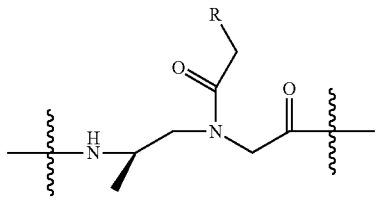

Figure 5:
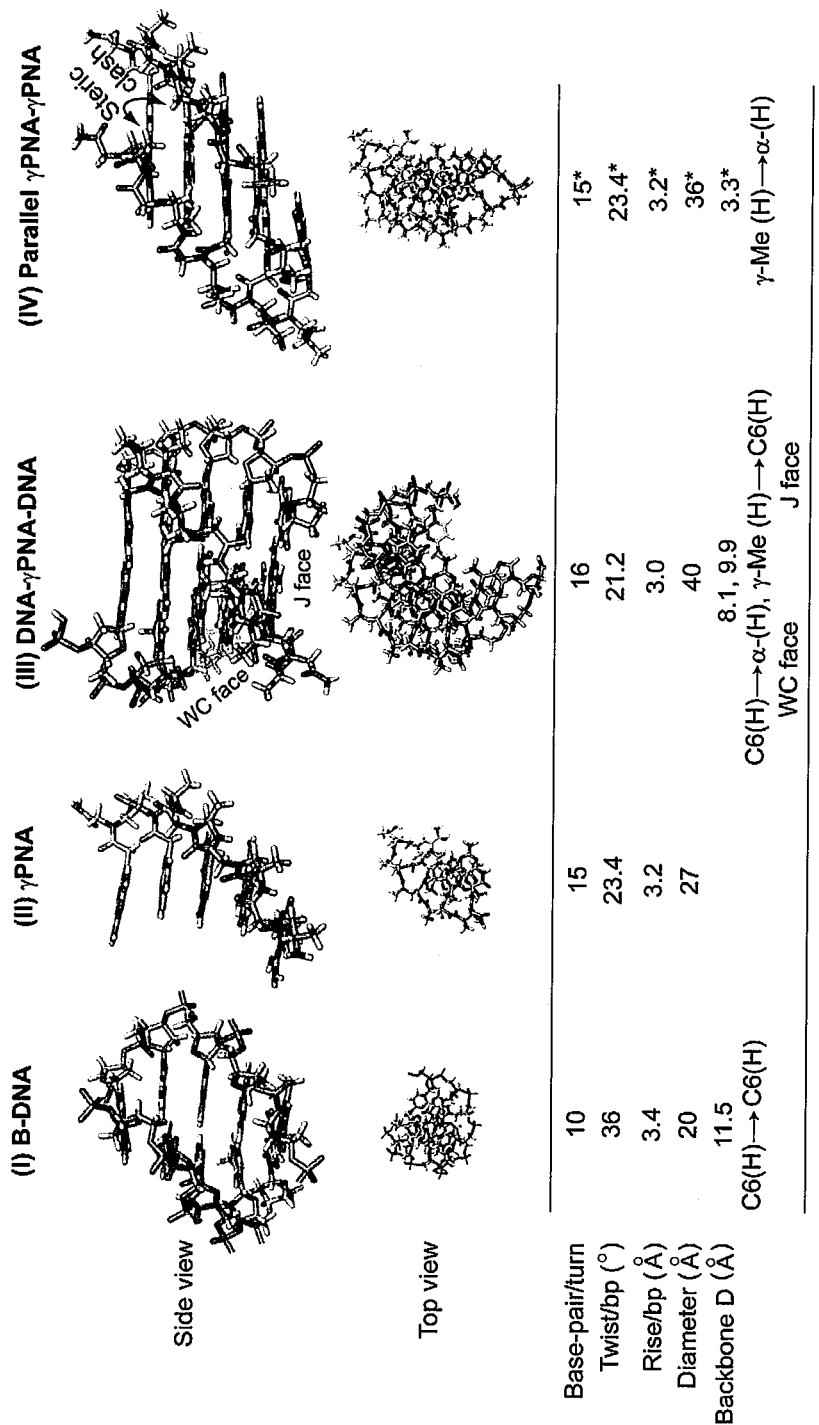
FIG. 5 illustrates simulated structures γPNAJB1-4 invading DNA double helix.

FIG. 5 illustrates the simulated structures of γPNAJB1-4 invading DNA double helix.

Figure 6:
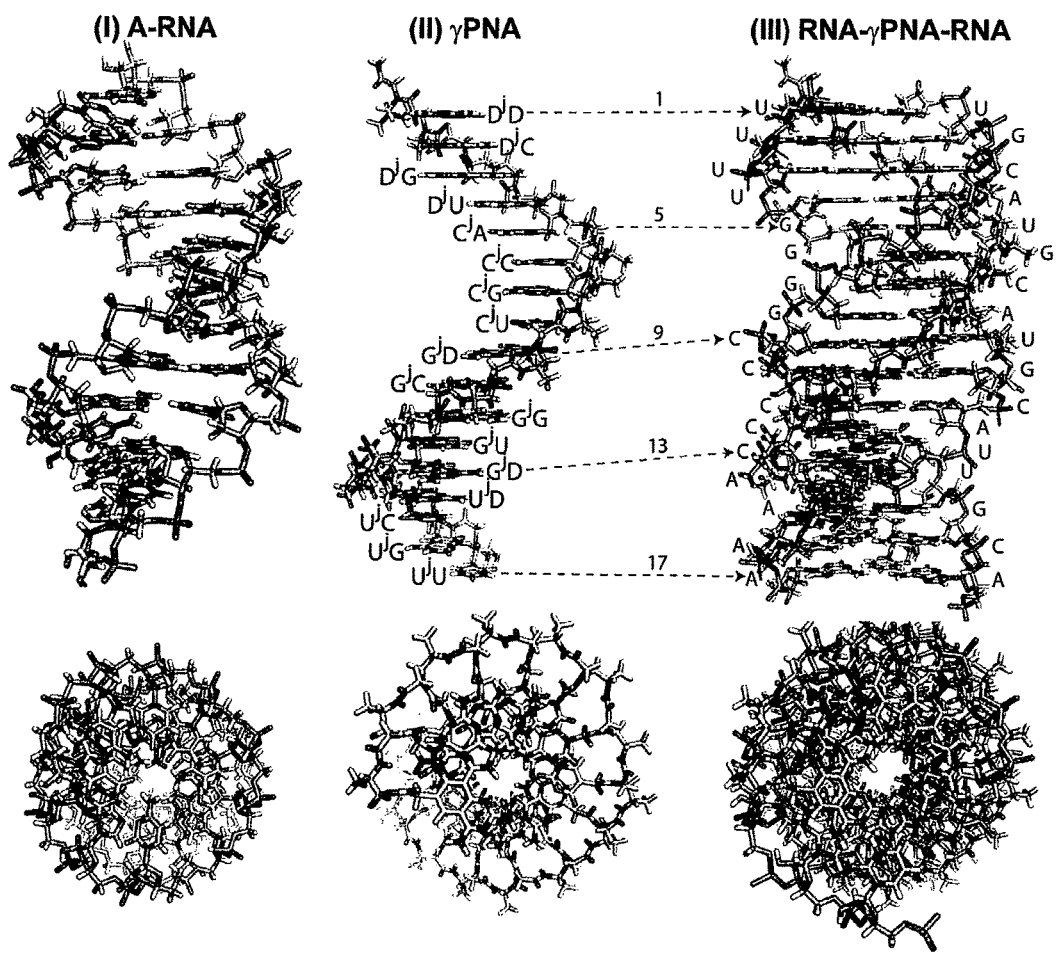
FIG. 6 illustrates simulated structures of γPNAJB1-16 invading an RNA secondary structure containing perfectly-matched and mismatched base-pairs.

FIG. 6 illustrates the structures of γPNAJB1-16 invading an RNA secondary structure containing perfectly-matched and mismatched base-pairs.

Example 2

Synthesis of Divalent Nucleobases, Nucleotide Monomers and γPNA Oligomers

Figure 7:
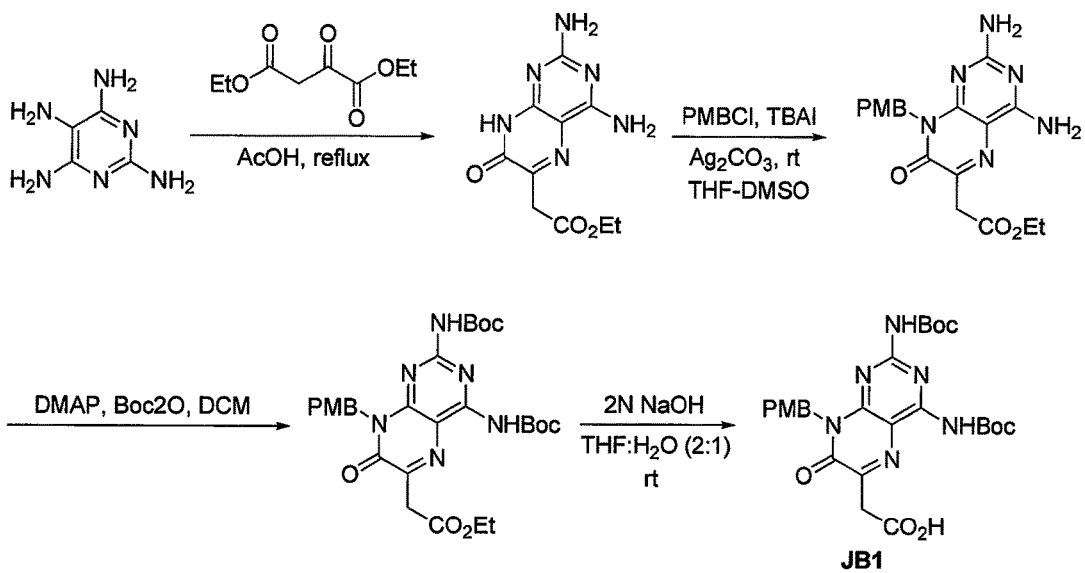
FIG. 7 illustrates exemplary schemes for synthesis of the described divalent nucleobases.
Figure 7:
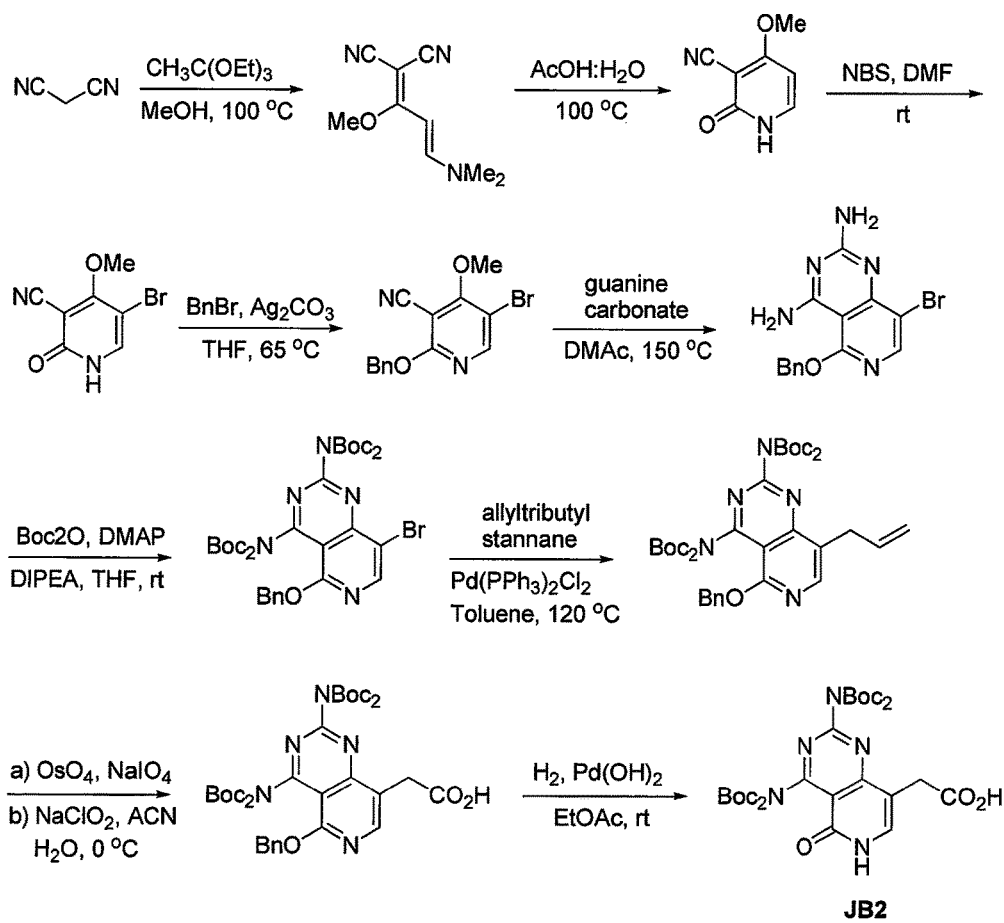
Figure 7:
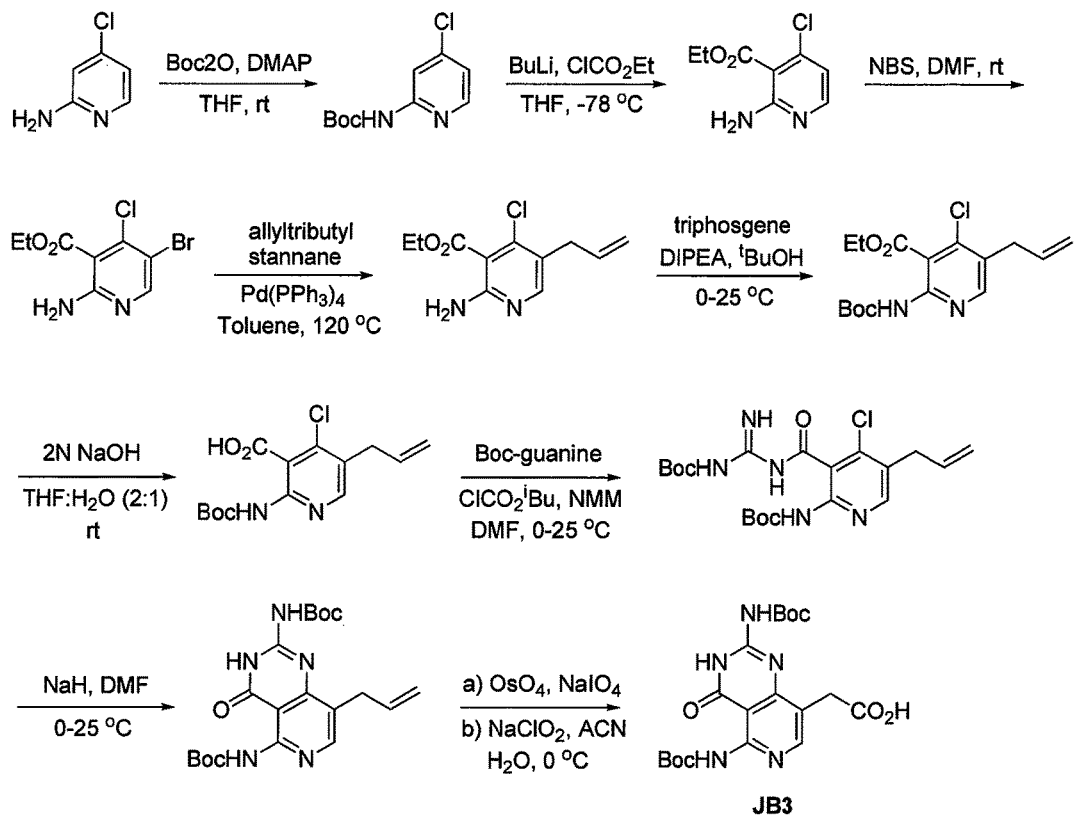
Figure 7:
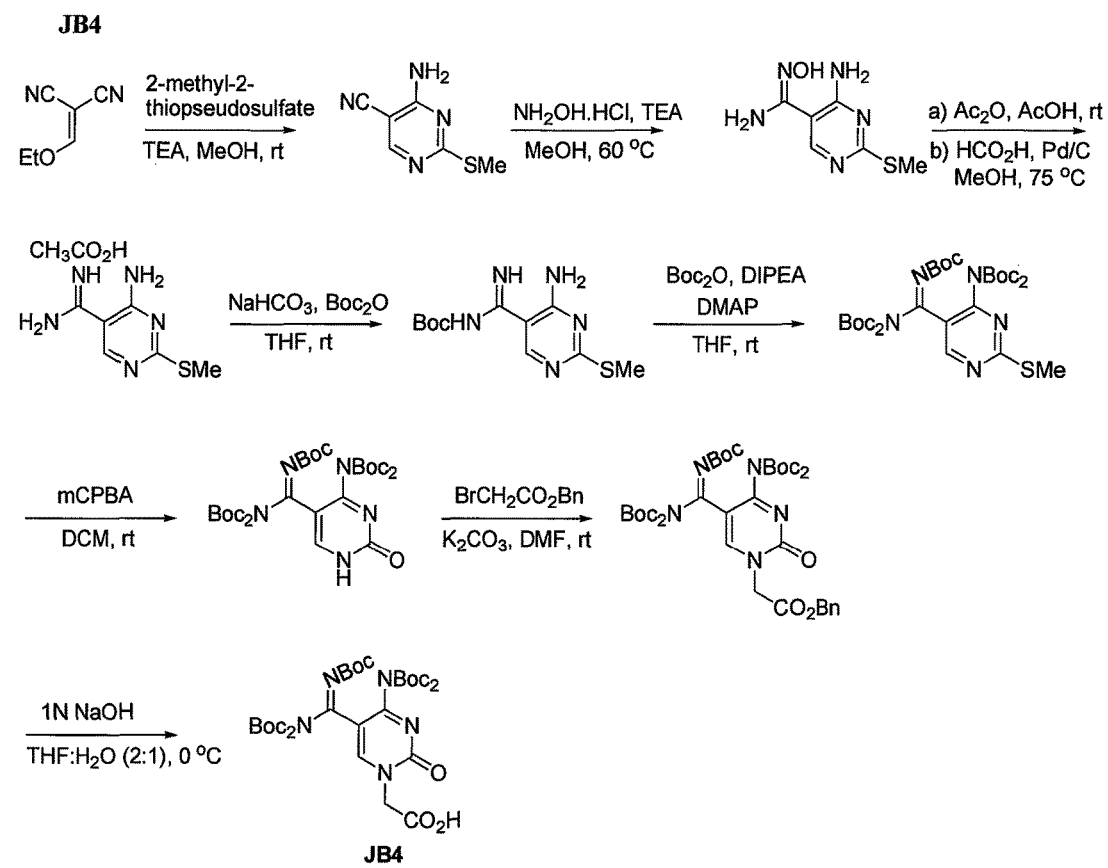
Figure 7:
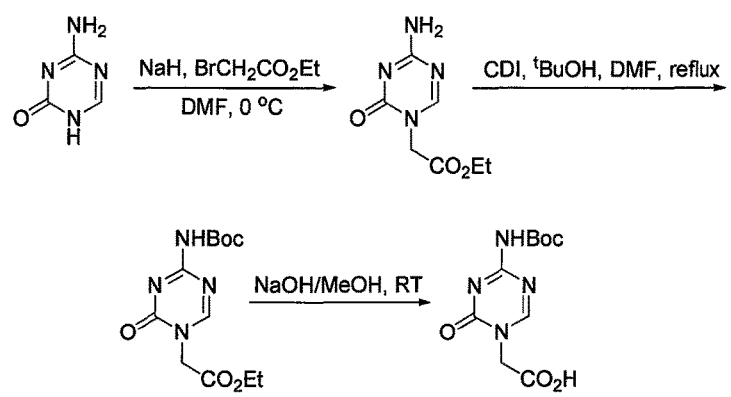
Figure 7:
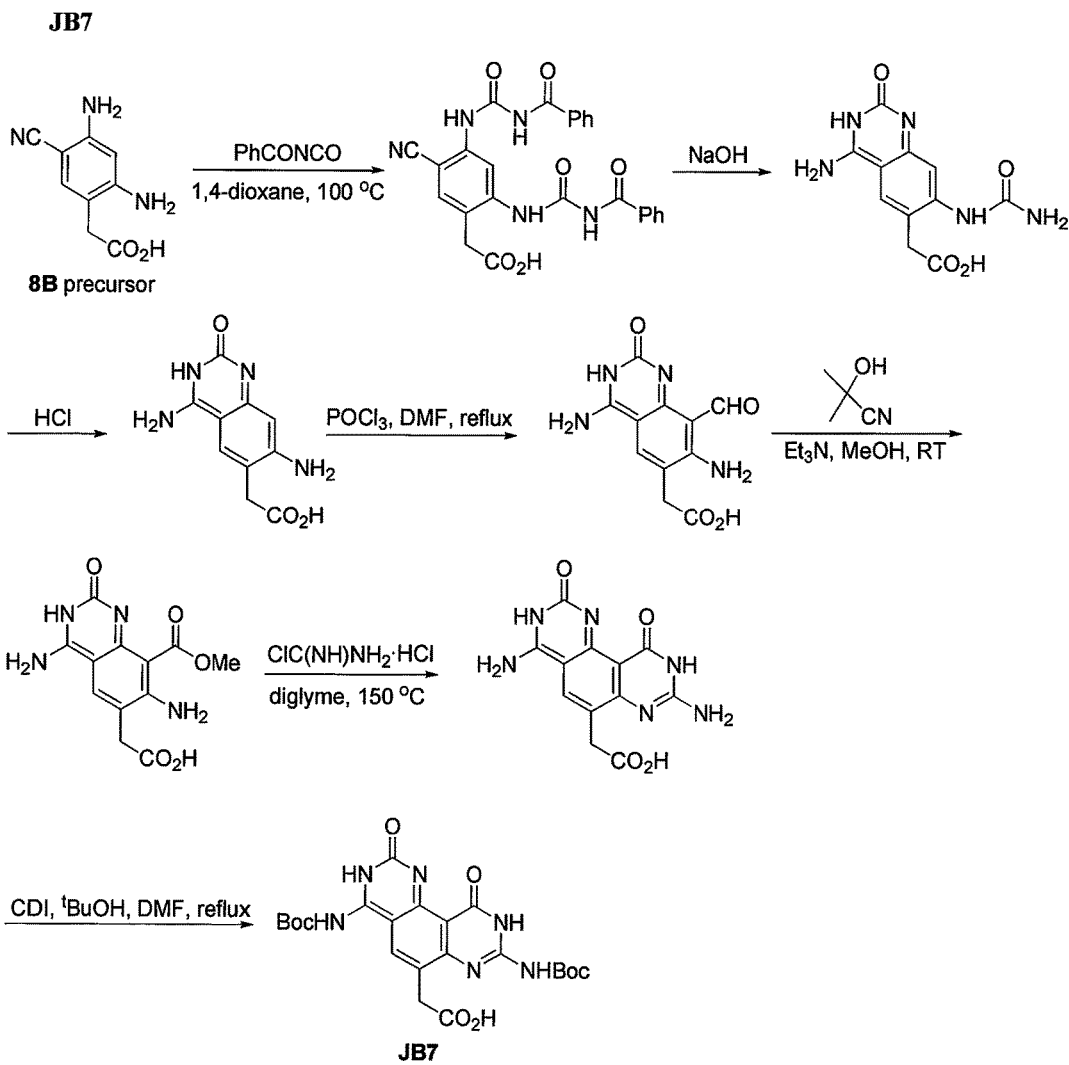
Figure 7:
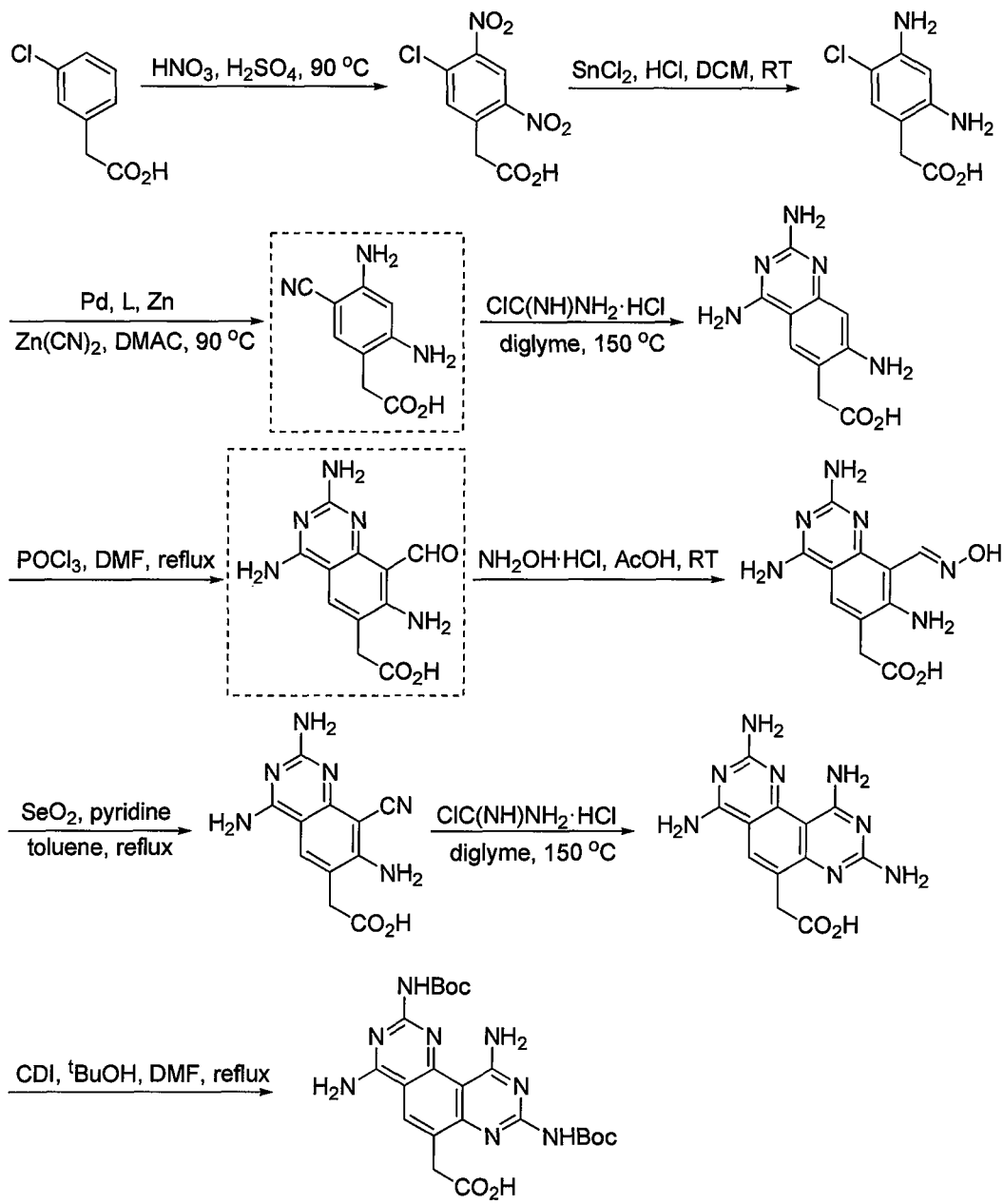
Figure 7:
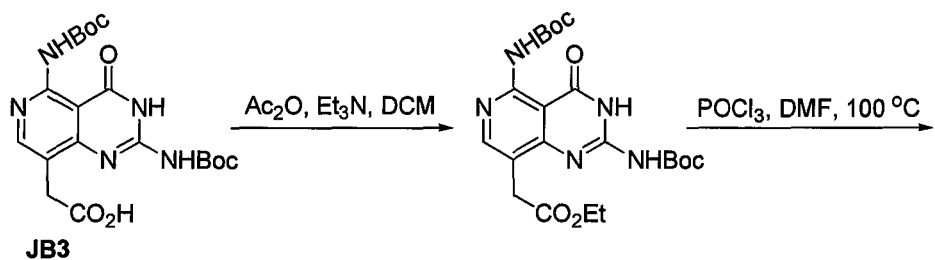
Figure 7:
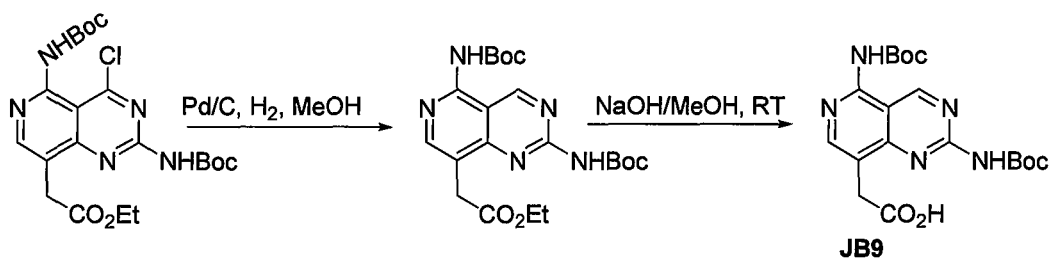
Figure 7:
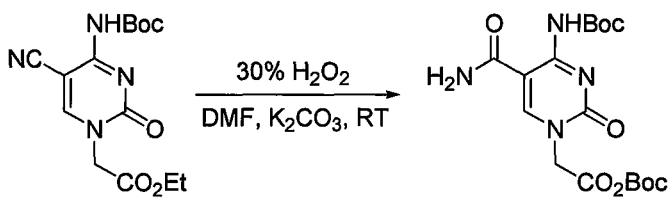
Figure 7:
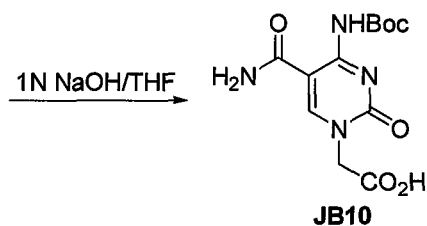
Figure 7:
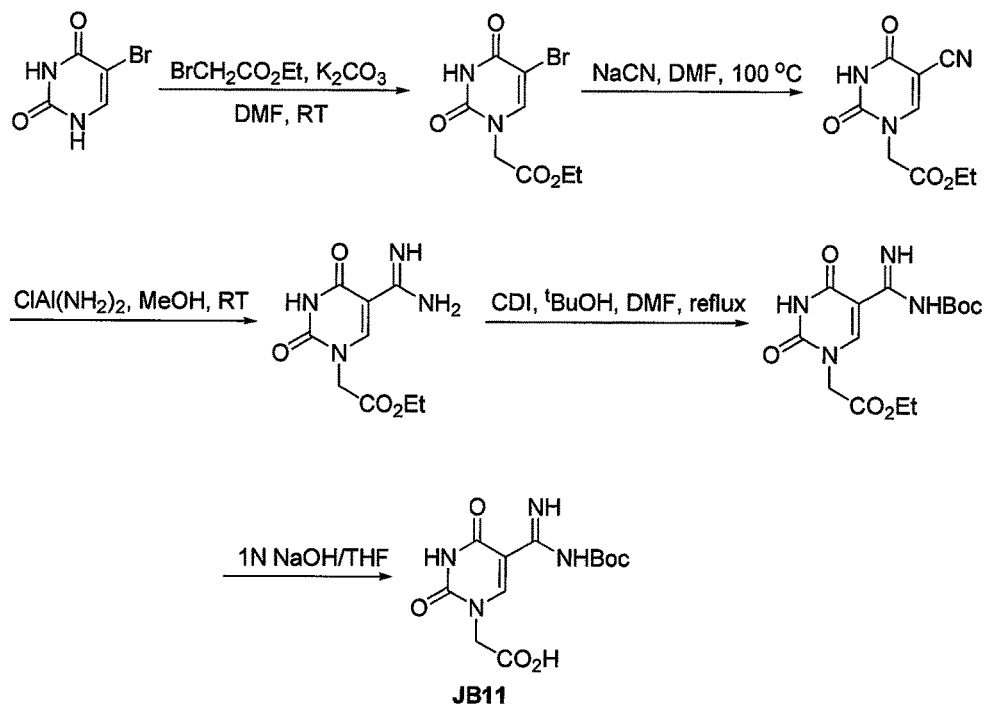
Figure 7:
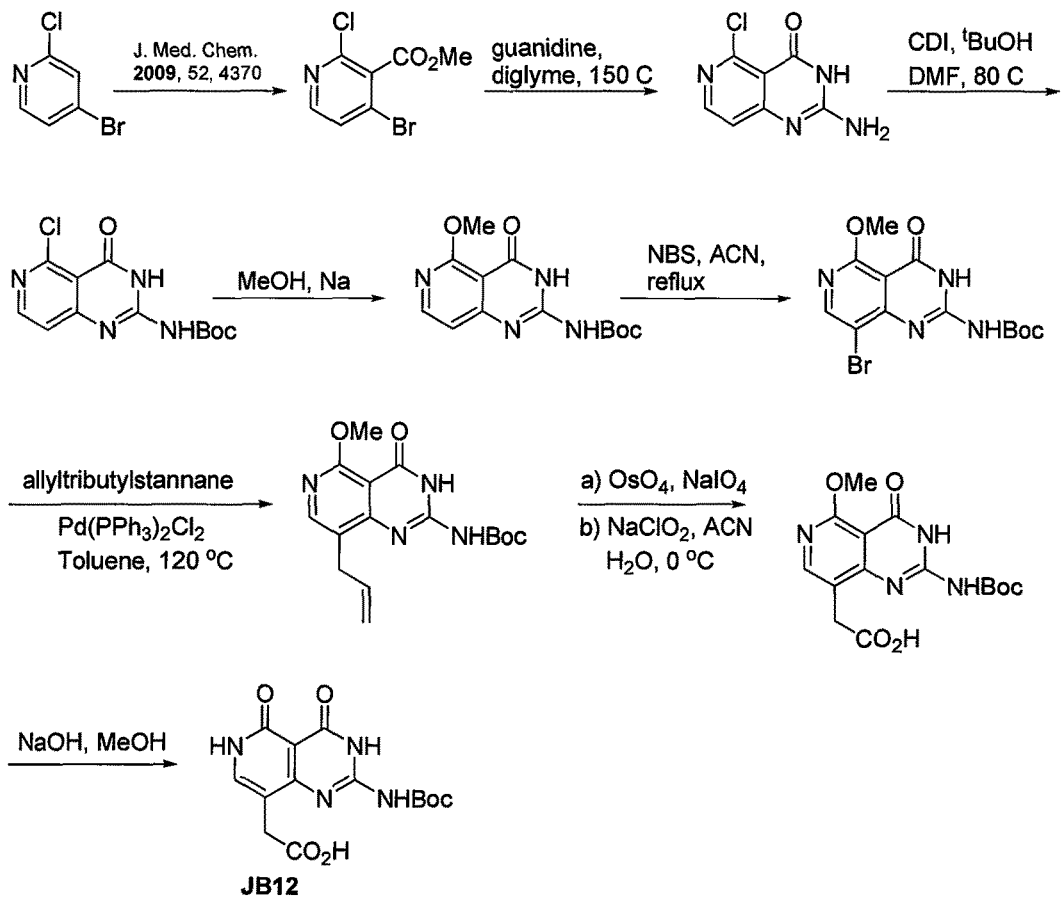
Figure 7:
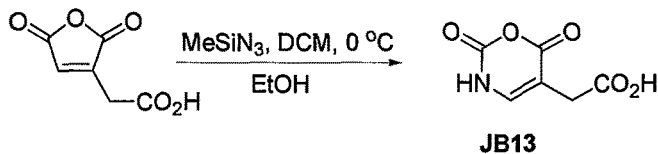
Figure 7:
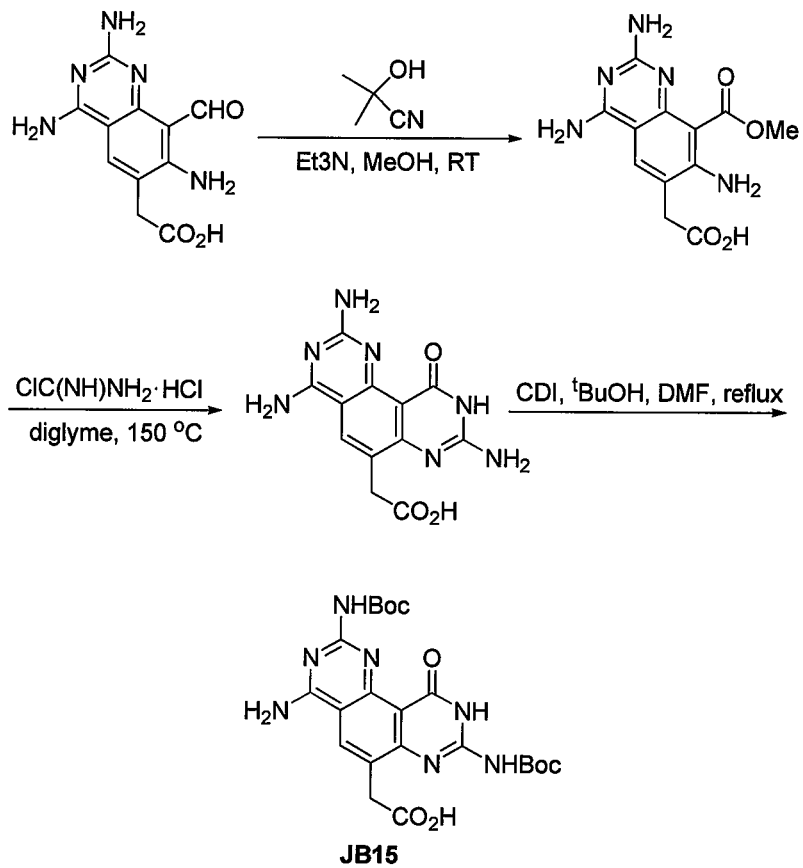
Figure 7:
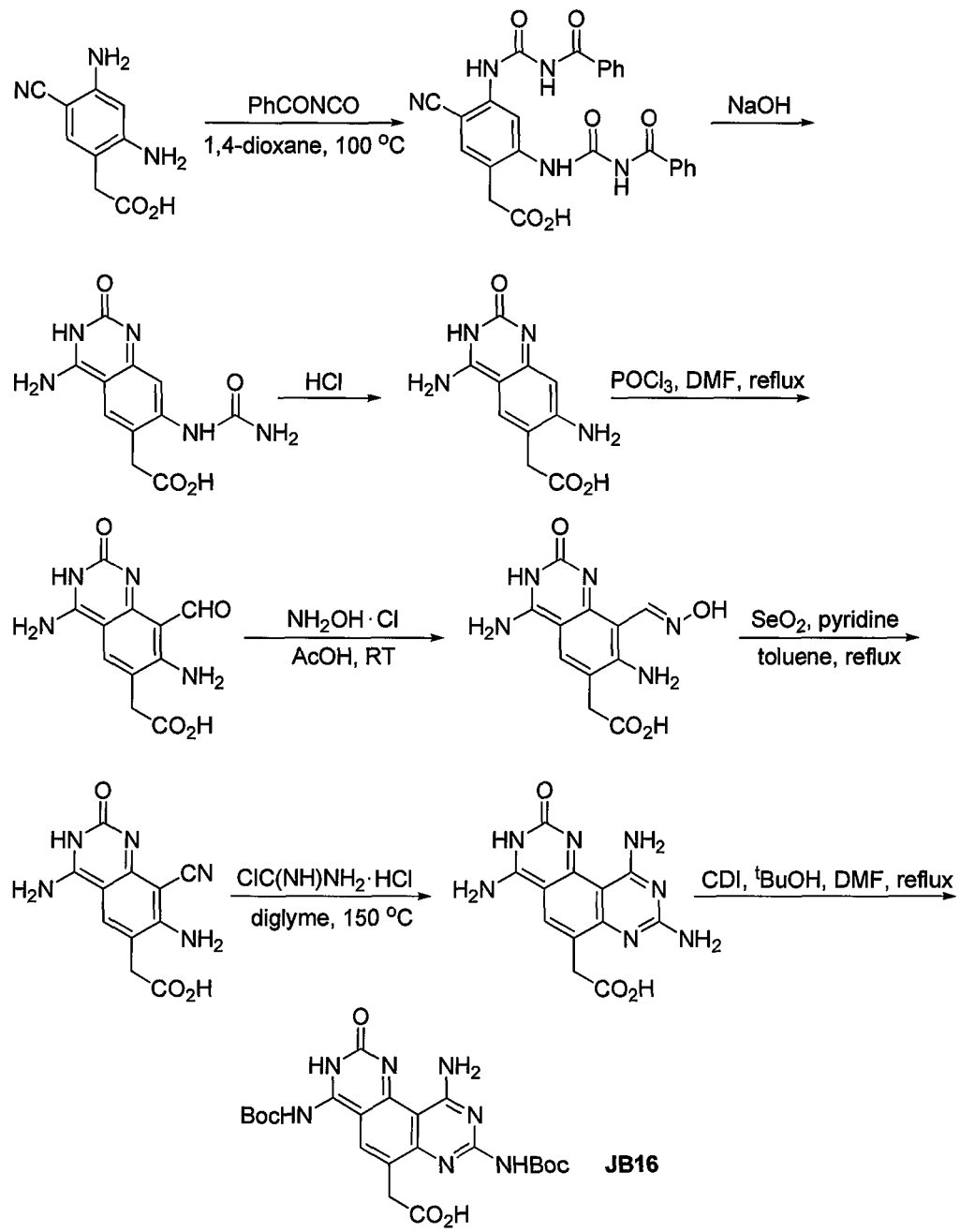
Figure 8:
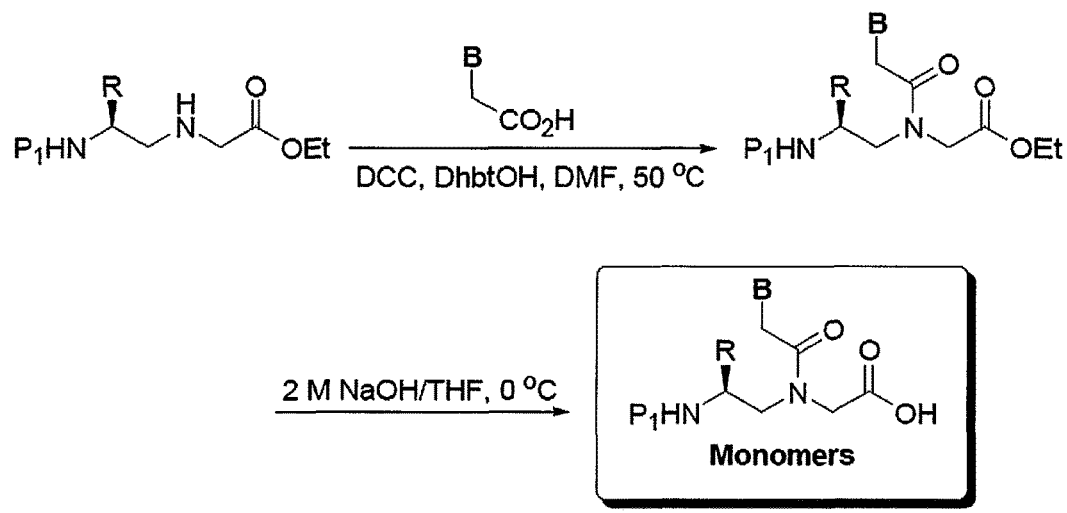
FIG. 8 illustrates an exemplary scheme for the synthesis of γPNA monomers with divalent nucleobases.
Figure 9:
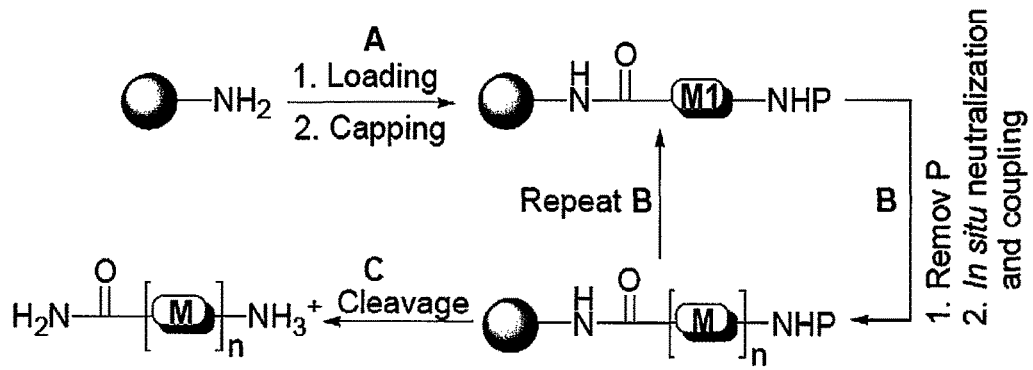
FIG. 9 illustrates an exemplary scheme for synthesis of γPNA oligomers with divalent nucleobases.

Examples of reactions performed to synthesis JBs 1-16 are shown in FIG. 7. Upon synthesis of these specialized bases, the corresponding monomers can be synthesized and an example synthesis scheme is described in FIG. 8. FIG. 9 illustrates the synthesis of oligomers containing the γPNA oligomers.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

We claim:

1. A genetic recognition reagent comprising a plurality of nucleobase residues attached to a nucleic acid or nucleic acid analog backbone, in which at least one nucleobase residue is a divalent nucleobase chosen from the following:

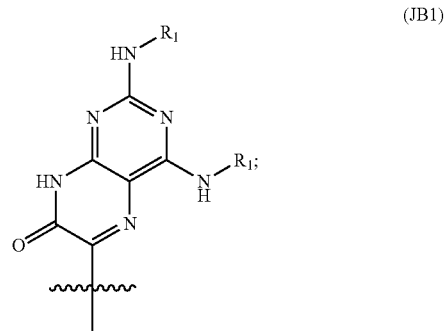

(JB1)

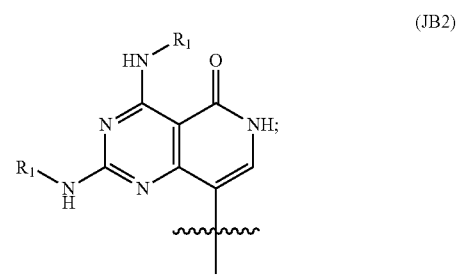

(JB2)

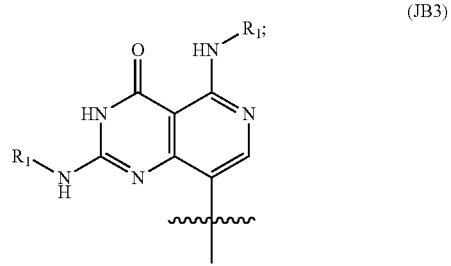

(JB3)

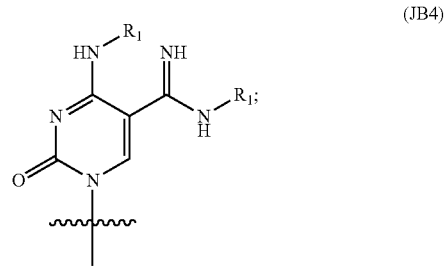

(JB4)

(JB7)
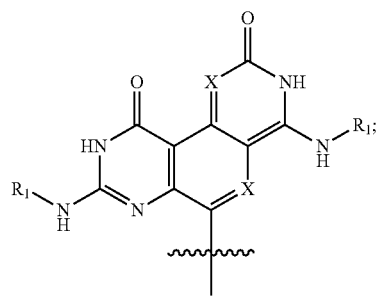
(JB8)
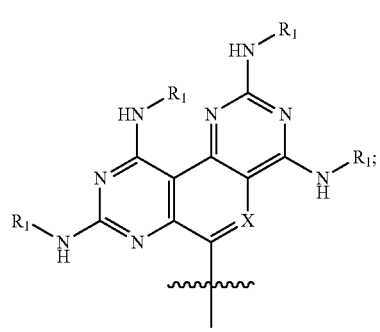
(JB9)
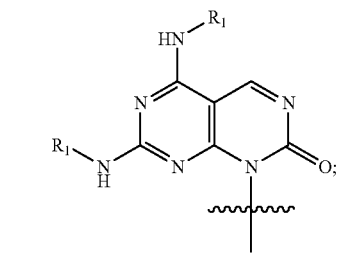
(JB9b)
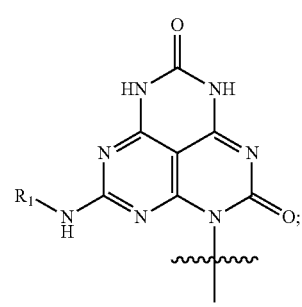
(JB10)
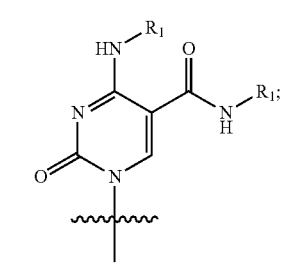
(JB11)
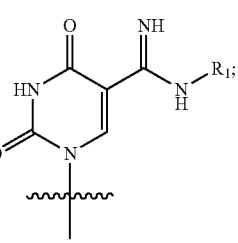
(JB12)
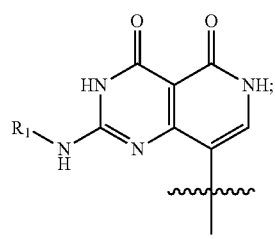
(JB13)
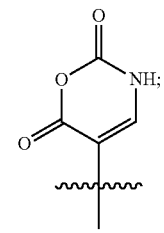
(JB14)
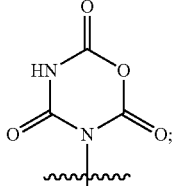
(JB15)
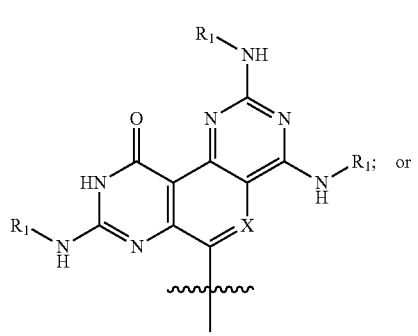
(JB16)
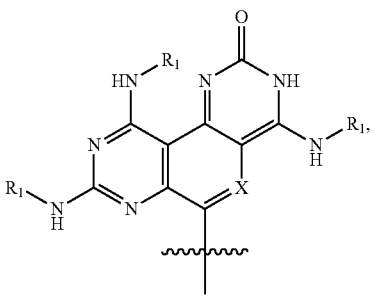
in which each instance of $R_1$ is, independently, a protecting group or H and X is CH or N.

2. The genetic recognition reagent of claim 1, in which each instance of $R_1$ is, independently, H or a protecting group chosen from: methyl, formyl, ethyl, acetyl, anisyl, benzyl, benzoyl, carbamate, trifluoroacetyl, diphenylmethyl, triphenylmethyl, N-hydroxysuccinimide, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethozybenzyl, p-methoxyphenyl, 4-toluenesulfonyl, p-nitrobenzenesulfonates, 9-fluorenylmethyloxycarbonyl, 2-nitrophenylsulfenyl, 2,2,5,7,8-pentamethyl-chroman-6-sulfonyl, and p-bromobenzenesulfonyl.

3. The genetic recognition reagent of claim 1, in which the backbone is chosen from one of a DNA, RNA, peptide nucleic acid (PNA), phosphorothioate, locked nucleic acid, unlocked nucleic acid, 2'-O-methyl-substituted RNA, morpholino nucleic acid, threose nucleic acid, or glycol nucleic acid backbone, or any combination thereof.

4. The genetic recognition reagent of claim 1, in which the backbone is a peptide nucleic acid (PNA) backbone.

5. The genetic recognition reagent of claim 1, in which the backbone is a gamma peptide nucleic acid (γPNA) backbone.

6. The genetic recognition reagent of claim 5, in which the backbone is PEGylated, with one or more PEG moieties of two to fifty (—O—CH$_2$—CH$_2$—) residues.

7. The genetic recognition reagent of claim 1, in which the backbone is a γPNA backbone in which a backbone monomer residue of the γPNA backbone is

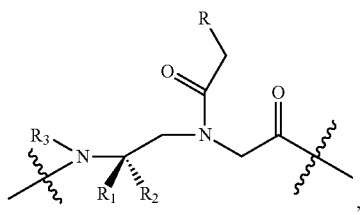

wherein R is a nucleobase residue, $R_1$ of the backbone monomer residue, $R_2$ and $R_3$ are, independently, H, amino acid side chains, linear or branched (C$_1$-C$_8$)alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$)cycloalkyl, (C$_3$-C$_8$)aryl(C$_1$-C$_6$)alkylene, (C$_3$-C$_8$)cycloalkyl(C$_1$-C$_6$)alkylene, PEGylated moieties of the preceding comprising from 1 to 50 (—O—CH$_2$—CH$_2$—) residues, —CH$_2$—(OCH$_2$—CH$_2$)$_q$OP$_1$, —CH$_2$—(OCH$_2$—CH$_2$)$_q$—NHP$_1$, —CH$_2$—(OCH$_2$—CH$_2$)$_q$—SP$_1$ and —CH$_2$—(SCH$_2$—CH$_2$)$_q$—SP$_1$, —CH$_2$—(OCH$_2$—CH$_2$)$_r$—OH, —CH$_2$—(OCH$_2$—CH$_2$)$_r$—NH$_2$, —CH$_2$—(OCH$_2$—CH$_2$)$_r$—NHC(NH)NH$_2$, or —CH$_2$—(OCH$_2$—CH$_2$)$_r$—S—S[CH$_2$CH$_2$]$_s$NHC(NH)NH$_2$, where P$_1$ is selected from the group consisting of H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene and (C$_3$-C$_8$)cycloalkyl(C$_1$-C$_6$)alkylene; q is an integer from 0 to 10, inclusive; r and s are each independently integers from 1 to 50, inclusive; where $R_1$ of the backbone monomer residue and $R_2$ are different and one of $R_1$ of the backbone monomer residue or $R_2$ is H.

8. The genetic recognition reagent of claim 7, in which $R_2$ is H, $R_1$ of the backbone monomer residue is an amino acid side chain that is optionally PEGylated, with one or more PEG moieties of one to twelve (—O—CH$_2$—CH$_2$—) residues.

9. The genetic recognition reagent of claim 1, in which the nucleobase residues are arranged in a sequence complementary to a target sequence of a nucleic acid.

10. The genetic recognition reagent of claim 1, having from 3 to 25 nucleobase residues.

11. The genetic recognition reagent of claim 1, having the structure:

where each instance of $R_4$ is a backbone monomer residue and each instance of R is one of the plurality of nucleobase residues, where at least one instance of R the divalent nucleobase, E are independently end groups, and "n" is zero or a positive integer ranging from 1 to 48, wherein the plurality of nucleobase residues forms a sequence that is complementary to a target sequence of a nucleic acid.

12. The genetic recognition reagent of claim 1, in which the divalent nucleobase is chosen from JB1, JB2, JB3, or JB4.

13. The genetic recognition reagent of claim 1, in which all instances of $R_1$ are H.

14. A monomer for production of a genetic recognition reagent comprising a backbone monomer for a genetic recognition reagent covalently attached to a divalent nucleobase chosen from the following:

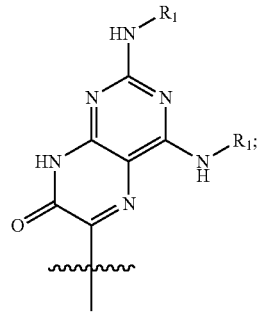
(JB1)

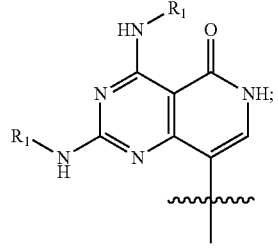
(JB2)

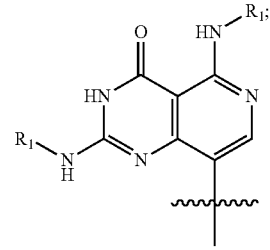
(JB3)

-continued
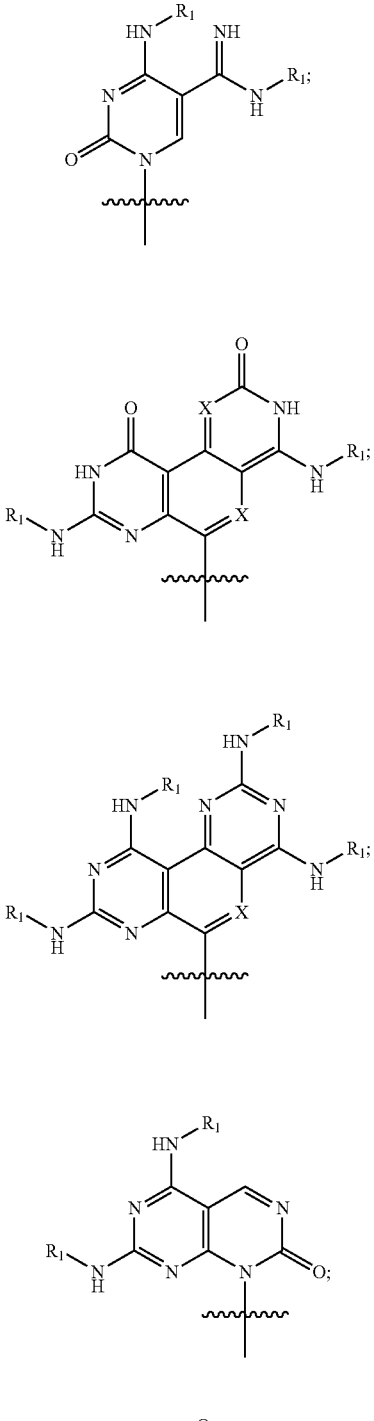
(JB4)
(JB7)
(JB8)
(JB9)
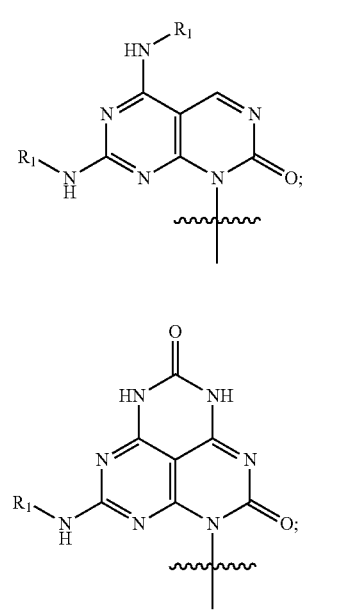
(JB9b)
-continued
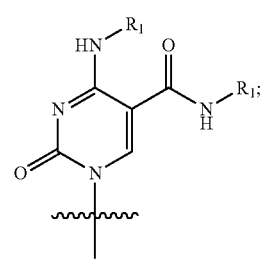
(JB10)
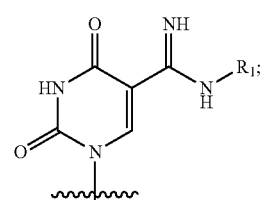
(JB11)
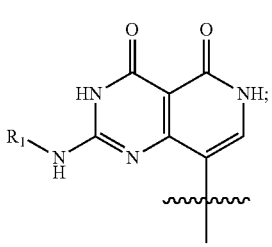
(JB12)
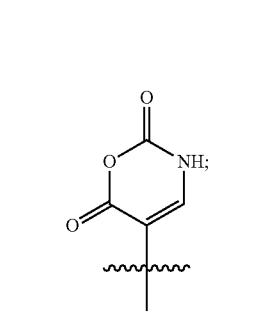
(JB13)
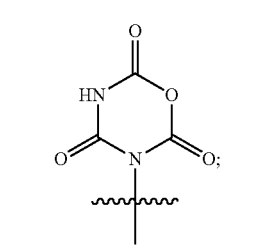
(JB14)
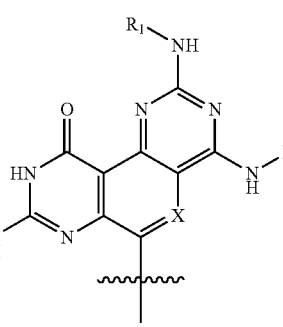
(JB15)

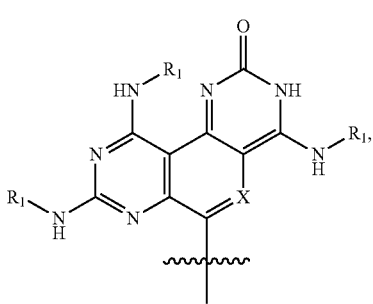

(JB16)

in which each instance of $R_1$ is, independently, a protecting group or H and X is CH or N.

15. The monomer of claim 14, in which the nucleobase is one of JB1, JB2, JB3 or JB4.

16. The monomer of claim 14, in which $R_1$ is a protecting group.

17. The monomer of claim 16, in which the protecting group is chosen from one or more of: methyl, formyl, ethyl, acetyl, anisyl, benzyl, benzoyl, carbamate, trifluoroacetyl, diphenylmethyl, triphenylmethyl, N-hydroxysuccinimide, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethozybenzyl, p-methoxyphenyl, 4-toluenesulfonyl, p-nitrobenzenesulfonates, 9-fluorenylmethyloxycarbonyl, 2-nitrophenylsulfenyl, 2,2,5,7,8-pentamethyl-chroman-6- sulfonyl, and p-bromobenzenesulfonyl.

18. The monomer of claim 14, in which the monomer is a peptide nucleic acid (PNA) monomer.

19. The monomer of claim 14, in which the monomer is a gamma peptide nucleic acid (γPNA) backbone monomer.

20. The monomer of claim 14, in which the backbone monomer is PEGylated, with one or more PEG moieties of two to fifty (—O—CH$_2$—CH$_2$—) residues.

21. The monomer of claim 14, in which the monomer is a γPNA monomer having the structure:

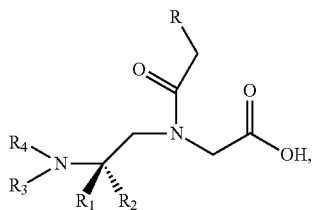

wherein R is a nucleobase residue, $R_1$ of the γPNA monomer, $R_2$ and $R_4$ are, independently, H, amino acid side chains, linear or branched ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, PEGylated moieties of the preceding comprising from 1 to 50 (—O—CH$_2$—CH$_2$—) residues, —CH$_2$—(OCH$_2$—CH$_2$)$_q$OP$_1$, —CH$_2$—(OCH$_2$—CH$_2$)$_q$—NHP$_1$, —CH$_2$—(OCH$_2$—CH$_2$)$_q$—SP$_1$ and —CH$_2$—(SCH$_2$—CH$_2$)$_q$—SP$_1$, —CH$_2$—(OCH$_2$—CH$_2$)$_r$—OH, —CH$_2$—(OCH$_2$—CH$_2$)$_r$—NH$_2$, —CH$_2$—(OCH$_2$—CH$_2$)$_r$—NHC(NH)NH$_2$, or —CH$_2$—(OCH$_2$—CH$_2$)$_r$—S—S[CH$_2$CH$_2$]$_s$NHC(NH)NH$_2$, where $P_1$ is selected from the group consisting of H, ($C_1$-$C_8$)alkyl, ($C_2$-$C_8$)alkenyl, ($C_2$-$C_8$)alkynyl, ($C_3$-$C_8$)aryl, ($C_3$-$C_8$)cycloalkyl, ($C_3$-$C_8$)aryl($C_1$-$C_6$)alkylene and ($C_3$-$C_8$)cycloalkyl($C_1$-$C_6$)alkylene; q is an integer from 0 to 10, inclusive; r and s are each independently integers from 1 to 50, inclusive; where $R_1$ of the γPNA monomer and $R_2$ are different, and one of $R_1$ of the γPNA monomer or $R_2$ is H, and $R_3$ is H or a protecting group.

22. The monomer of claim 21, in which $R_2$ is H, $R_1$ of the γPNA monomer is an amino acid side chain that is optionally PEGylated, with one or more PEG moieties of one to twelve (—O—CH$_2$—CH$_2$—) residues, and $R_3$ is a protecting group.

23. A nucleobase chosen from one the following:

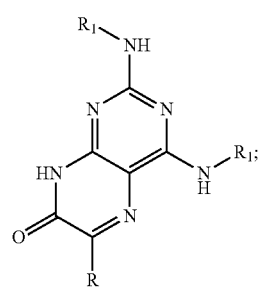

(JB1)

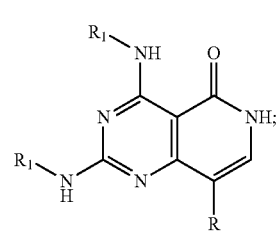

(JB2)

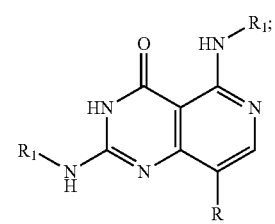

(JB3)

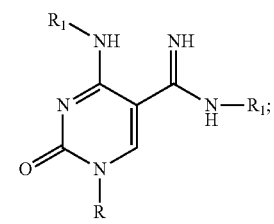

(JB4)

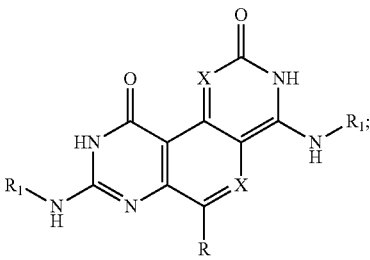

(JB7)

(JB8)
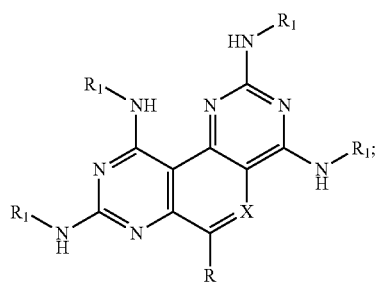
(JB9)
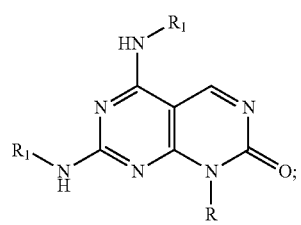
(JB9b)
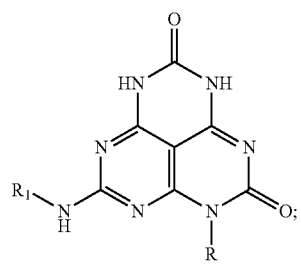
(JB10)
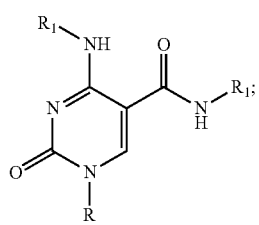
(JB11)
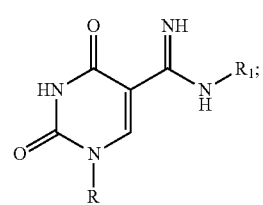
(JB12)
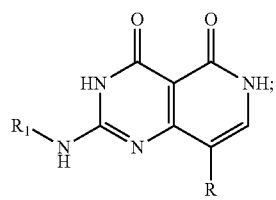
(JB13)
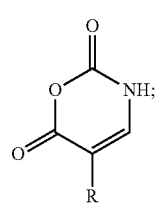
(JB14)
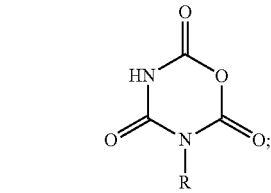
(JB15)
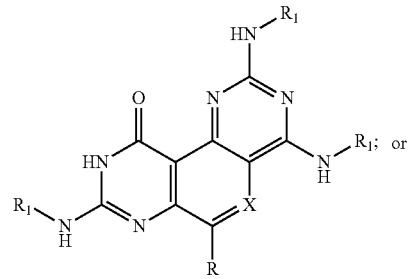
(JB16)
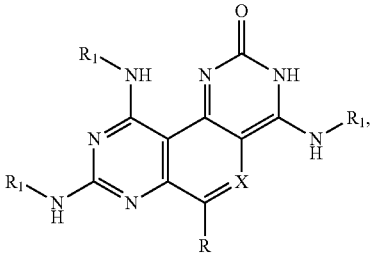
in which each instance of $R_1$ is, independently a protecting group or H, R is a reactive group and X is CH or N.
24. The nucleobase of claim 23, chosen from one of the following:
(JB7)
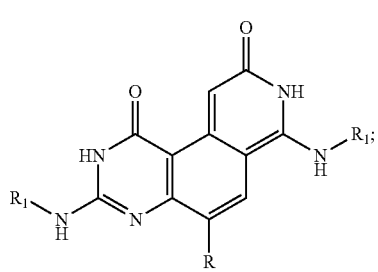
(JB8)
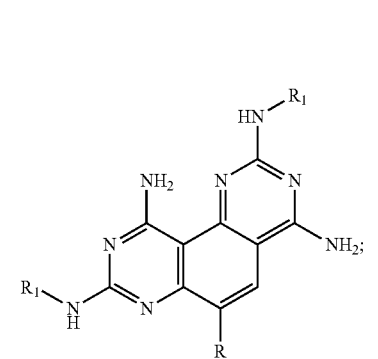

-continued

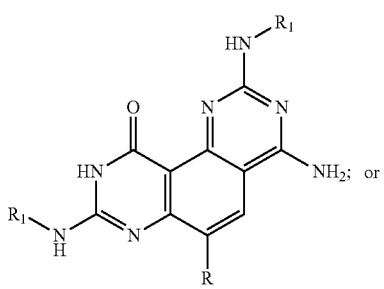
(JB15)

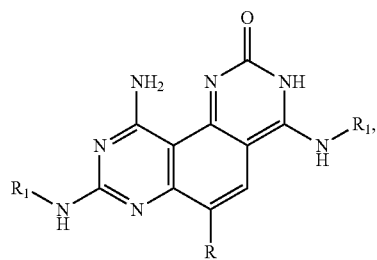
(JB16)

in which each instance of $R_1$ is, independently a protecting group or H.

25. A kit comprising a monomer of claim 14 in a vessel.

26. The kit of claim 25, further comprising monomers comprising each of JB1, JB2, JB3, JB4,

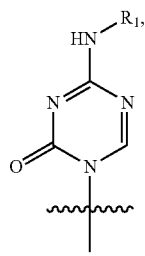
(JB5)

where $R_1$ is a protecting group, or H,

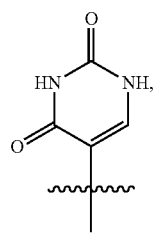
(JB6)

JB7, JB8, JB9, JB9b, JB10, JB11, JB12, JB13, JB14, JB15, and JB16 nucleobases in separate vessels.

27. An array comprising the genetic recognition reagent of claim 1.

28. A method of detection of a target sequence in a nucleic acid, comprising contacting the genetic recognition reagent of claim 1 with a sample comprising nucleic acid and detecting binding of the genetic recognition reagent with the nucleic acid.

29. A method of isolation and purification of a nucleic acid containing a target sequence, comprising, contacting a nucleic acid sample with the genetic recognition reagent of claim 1, separating the nucleic acid sample from the genetic recognition reagent, leaving any nucleic acid bound to the genetic recognition reagent bound to the genetic recognition reagent, and separating the genetic recognition reagent from any nucleic acid bound to the genetic recognition reagent.

30. The method of claim 29 in which the genetic recognition reagent is immobilized on a substrate, comprising contacting the nucleic acid with the substrate, washing the substrate to remove unbound nucleic acid from the substrate, but leaving bound nucleic acid bound to the substrate, and eluting the bound nucleic acid from the substrate.

31. The genetic recognition reagent of claim 1, wherein at least one nucleobase is JB1.

32. The genetic recognition reagent of claim 1, wherein at least one nucleobase is JB2.

33. The genetic recognition reagent of claim 1, wherein at least one nucleobase is JB3.

34. The genetic recognition reagent of claim 1, wherein at least one nucleobase is JB4.

35. A genetic recognition reagent comprising a plurality of nucleobase residues attached to a peptide nucleic acid backbone, in which at least one nucleobase is

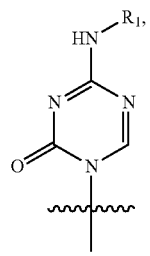
(JB5)

where $R_1$ is a protecting group, or H.

36. The genetic recognition reagent of claim 35, wherein the backbone is a gamma peptide nucleic acid (γPNA) backbone.

37. The monomer of claim 14, wherein the divalent nucleobase is JB1.

38. The monomer of claim 14, wherein the divalent nucleobase is JB2.

39. The monomer of claim 14, wherein the divalent nucleobase is JB3.

40. The monomer of claim 14, wherein the divalent nucleobase is JB4.

41. The nucleobase of claim 23, having the structure of JB1.

42. The nucleobase of claim 23, having the structure of JB2.

43. The nucleobase of claim 23, having the structure of JB3.

44. The nucleobase of claim 23, having the structure of JB4.

45. The nucleobase of claim 23, wherein R is carboxyl.

46. The kit of claim 25, wherein the monomer comprises a peptide nucleic acid backbone monomer.

47. The kit of claim 25, wherein the monomer comprises a γ-peptide nucleic acid backbone monomer.

* * * * *

UNITED STATES PATENT AND TRADEMARK OFFICE
CERTIFICATE OF CORRECTION

PATENT NO. : 10,370,415 B2
APPLICATION NO. : 14/782471
DATED : August 6, 2019
INVENTOR(S) : Danith H. Ly et al.

Page 1 of 1

It is certified that error appears in the above-identified patent and that said Letters Patent is hereby corrected as shown below:

On the Title Page

Item (57), Column 2, Lines 4-5, delete "(a genetic recognition reagent, or genetic recognition reagent)." and insert -- (a genetic recognition reagent). --

Item (57), Column 2, Line 7, delete "(?PNA)" and insert -- (γPNA) --

In the Claims

Column 31, Line 11, Claim 2, delete "3,4-dimethozybenzyl," and insert -- 3, 4-dimethoxybenzyl, --

Column 31, Line 47, Claim 7, delete "$R_2$and $R_3$" and insert -- $R_2$ and $R_3$ --

Column 31, Line 65, Claim 7, delete "$R_2$is H." and insert -- $R_2$ is H. --

Column 32, Line 18, Claim 11, after "R" insert -- is --

Column 35, Line 32, Claim 17, delete "3,4-dimethozybenzyl," and insert -- 3, 4-dimethoxybenzyl, --

Column 36, Line 16, Claim 23, after "one" insert -- of --

Signed and Sealed this
Thirty-first Day of March, 2020

Andrei Iancu
*Director of the United States Patent and Trademark Office*